United States Patent
Gordillo et al.

(10) Patent No.: US 10,774,034 B2
(45) Date of Patent: Sep. 15, 2020

(54) PROCESS FOR THE CONVERSION OF ETHYLENE OXIDE TO MONOETHANOLAMINE AND ETHYLENEDIAMINE EMPLOYING A ZEOLITE

(71) Applicant: BASF SE, Ludwigshafen am Rhein (DE)

(72) Inventors: Alvaro Gordillo, Ludwigshafen am Rhein (DE); Andrei-Nicolae Parvulescu, Ludwigshafen am Rhein (DE); Armin Lange De Oliveira, Heidelberg (DE); Andreas Kuschel, Heidelberg (DE); Juergen Bechtel, Heidelberg (DE); Johannes Lieberknecht, Heidelberg (DE); Ulrich Müller, Ludwigshafen am Rhein (DE); Johann-Peter Melder, Ludwigshafen am Rhein (DE); Christian Gruenanger, Ludwigshafen am Rhein (DE)

(73) Assignee: BASF SE (DE)

( * ) Notice: Subject to any disclaimer, the term of this patent is extended or adjusted under 35 U.S.C. 154(b) by 0 days.

(21) Appl. No.: 16/610,131

(22) PCT Filed: May 3, 2018

(86) PCT No.: PCT/EP2018/061326
§ 371 (c)(1),
(2) Date: Nov. 1, 2019

(87) PCT Pub. No.: WO2018/202765
PCT Pub. Date: Nov. 8, 2018

(65) Prior Publication Data
US 2020/0087246 A1    Mar. 19, 2020

(30) Foreign Application Priority Data

May 3, 2017  (EP) .................................. 17169221

(51) Int. Cl.
| | |
|---|---|
| *C07C 213/04* | (2006.01) |
| *B01J 29/24* | (2006.01) |
| *B01J 29/40* | (2006.01) |
| *B01J 29/70* | (2006.01) |
| *C07C 215/08* | (2006.01) |
| *B01J 37/30* | (2006.01) |
| *C01B 39/26* | (2006.01) |
| *C01B 39/38* | (2006.01) |
| *C07C 211/10* | (2006.01) |
| *B01J 37/08* | (2006.01) |

(52) U.S. Cl.
CPC ............ *C07C 213/04* (2013.01); *B01J 29/24* (2013.01); *B01J 29/40* (2013.01); *B01J 29/405* (2013.01); *B01J 29/70* (2013.01); *B01J 37/08* (2013.01); *B01J 37/30* (2013.01); *C01B 39/26* (2013.01); *C01B 39/38* (2013.01); *C07C 211/10* (2013.01); *C07C 215/08* (2013.01); *B01J 2229/186* (2013.01)

(58) Field of Classification Search
None
See application file for complete search history.

(56) References Cited

U.S. PATENT DOCUMENTS

| | | | |
|---|---|---|---|
| 4,918,233 | A | 4/1990 | Deeba et al. |
| 4,939,301 | A | 7/1990 | Grice et al. |
| 7,687,423 | B2 | 3/2010 | Moscoso et al. |
| 8,309,771 | B2 | 11/2012 | Noronha et al. |
| 10,202,323 | B2 | 2/2019 | Parvulescu et al. |
| 10,202,324 | B2 | 2/2019 | Vautravers et al. |
| 10,308,580 | B2 | 6/2019 | Rudenauer et al. |
| 2003/0149305 | A1 | 8/2003 | Frauenkron et al. |
| 2018/0215724 | A1 | 8/2018 | Gordillo et al. |
| 2018/0243691 | A1 | 8/2018 | Mueller et al. |
| 2018/0311611 | A1 | 11/2018 | Vorberg et al. |
| 2018/0319758 | A1 | 11/2018 | Gordillo et al. |
| 2018/0319759 | A1 | 11/2018 | Gordillo et al. |
| 2018/0328601 | A1 | 11/2018 | Weickert et al. |
| 2018/0333696 | A1 | 11/2018 | Burckhart et al. |
| 2018/0345245 | A1 | 12/2018 | Maurer et al. |
| 2018/0362351 | A1 | 12/2018 | Parvulescu et al. |
| 2018/0362353 | A1 | 12/2018 | Vautravers et al. |
| 2018/0362357 | A1 | 12/2018 | Feyen et al. |
| 2019/0077779 | A1 | 3/2019 | Riedel et al. |
| 2019/0134564 | A1 | 5/2019 | Feyen et al. |
| 2019/0143272 | A1 | 5/2019 | Trukhan et al. |
| 2019/0144290 | A1 | 5/2019 | Marx et al. |

(Continued)

FOREIGN PATENT DOCUMENTS

| | | |
|---|---|---|
| CN | 1962058 A | 5/2007 |
| CN | 101215239 B | 7/2010 |

(Continued)

OTHER PUBLICATIONS

International Preliminary Report on Patentability for PCT/EP2018/061326 dated Jul. 24, 2019.

(Continued)

*Primary Examiner* — Sudhakar Katakam
*Assistant Examiner* — Jennifer C Sawyer
(74) *Attorney, Agent, or Firm* — Faegre Drinker Biddle & Reath LLP

(57) ABSTRACT

The present invention relates to a process for the conversion of ethylene oxide to 2-aminoethanol and/or ethane-1,2-diamine and/or linear polyethylenimines of the formula $H_2N-(CH_2CH_2NH)_n-CH_2CH_2-NH_2$ wherein $n \geq 1$ comprising (i) providing a catalyst comprising a zeolitic material comprising $YO_2$ and $X_2O_3$, wherein Y is a tetravalent element and X is a trivalent element; (ii) providing a gas stream comprising ethylene oxide and ammonia; (iii) contacting the catalyst provided in (i) with the gas stream provided in (ii) for converting ethylene oxide to 2-aminoethanol and/or ethane-1,2-diamine and/or linear polyethylenimines.

14 Claims, No Drawings

(56) References Cited

U.S. PATENT DOCUMENTS

| | | |
|---|---|---|
| 2019/0169037 A1 | 6/2019 | Trukhan et al. |
| 2019/0169112 A1 | 6/2019 | Eidamshaus et al. |
| 2019/0169149 A1 | 6/2019 | Teles et al. |
| 2019/0210989 A1 | 7/2019 | Teles et al. |
| 2019/0233364 A1 | 8/2019 | De Oliveira et al. |
| 2019/0300375 A1 | 10/2019 | McGuire et al. |
| 2019/0308928 A1 | 10/2019 | Parvulescu et al. |
| 2019/0308929 A1 | 10/2019 | Parvulescu et al. |
| 2019/0321811 A1 | 10/2019 | Parvulescu et al. |
| 2019/0322634 A1 | 10/2019 | Teles et al. |
| 2019/0330171 A1 | 10/2019 | Parvulescu et al. |
| 2019/0359621 A1 | 11/2019 | Marion et al. |
| 2019/0366313 A1 | 12/2019 | McGuire et al. |
| 2019/0367377 A1 | 12/2019 | Parvulescu et al. |
| 2019/0389794 A1 | 12/2019 | Parvulescu et al. |
| 2020/0002255 A1 | 1/2020 | Parvulescu et al. |

FOREIGN PATENT DOCUMENTS

| | | |
|---|---|---|
| CN | 102190588 A | 9/2011 |
| CN | 102233272 A | 11/2011 |
| CN | 101406845 B | 2/2012 |
| CN | 102974393 A | 3/2013 |
| CN | 103007984 A | 4/2013 |
| DE | 298636 A5 | 3/1992 |
| JP | H0687797 A | 3/1994 |
| JP | H07247245 A | 9/1995 |
| WO | WO-2009083580 A1 | 7/2009 |
| WO | WO-2016135133 A1 | 9/2016 |
| WO | WO-2016180807 A1 | 11/2016 |
| WO | WO-2016180809 A1 | 11/2016 |
| WO | WO-2017076947 A1 | 5/2017 |
| WO | WO-2018007207 A1 | 1/2018 |
| WO | WO-2018046323 A1 | 3/2018 |

OTHER PUBLICATIONS

International Preliminary Report on Patentability for PCT/EP2018/061326 dated Jul. 3, 2018.

Feng, R., et al., "Shape-selctive amination of EO over HZSM-5 for MEA and DEA", Catalysis Communications, 2010, vol. 11, No. 15, pp. 1220-1223.

Fischer, Achim, "Heterogeneous Transition Metal Catalyzed Amination of Aliphatic Diols", Doctoral Thesis, 1998, 130 pages.

Vamling, L., et al., "Comparison of Some Solid Catalysts for the Production of Ethanolamines from Ammonia and Ethylene Oxide in the Liquid Phase", Industrial and Engineering Chemistry Product Reseach and Development, 1986, vol. 25, pp. 424-430.

U.S. Appl. No. 16/607,514, filed Oct. 23, 2019.

U.S. Appl. No. 16/500,313.

U.S. Appl. No. 16/499,686.

PROCESS FOR THE CONVERSION OF ETHYLENE OXIDE TO MONOETHANOLAMINE AND ETHYLENEDIAMINE EMPLOYING A ZEOLITE

CROSS-REFERENCE TO RELATED APPLICATIONS

This application is a national stage application (under 35 U.S.C. § 371) of PCT/EP2018/061326, filed May 3, 2018, which claims benefit of European Application No, 17169221.3, filed May 3, 2017, both of which are incorporated herein by reference in their entirety.

TECHNICAL FIELD

The present invention relates to a process for the conversion of ethylene oxide to 2-aminoethanol and/or ethane-1,2-diamine and/or linear polyethylenimines of the formula $H_2N-[CH_2CH_2NH]_n-CH_2CH_2NH_2$ wherein n≥1, said process employing a zeolitic material comprising $YO_2$ and $X_2O_3$, wherein Y is a tetravalent element and X is a trivalent element.

INTRODUCTION

Zeolite catalysts are known for the synthesis of ethylene amines by gas-phase amination of monoethanol amine (MEOA). Thus, U.S. Pat. No. 4,918,233 reports on the use of a rare-earth doped MOR for the monoethanol amine gas-phase amination to ethylenediamine (EDA) with 80% selectivity at 26% MEOA conversion. CN 1962058 A relates to the gas-phase synthesis of ethylenediamine, wherein the amination of monoethanol amine employs a Mordenite catalyst containing one of Zr, Nb, Mo, or Sn in combination with Zn or Fe. JP H0687797 A and JP H07247245 A respectively relate to a process for the gas-phase reaction of ammonia and monothanolamine to ethylenediamine with the use of a dealuminated Mordenite catalyst. Modification of the mordenite zeolite with P for production of EDA and piperazine derivates from MEOA is also described in CN 101215239 B. CN 101406845 A describes an H-mordenite amination catalyst and its preparation. CN 102974393 A relates to a method for regeneration of modified zeolite molecular sieve amination catalysts. CN 103007984 A claims a method for manufacturing amination catalysts. CN102233272 A and CN102190588 A a process for preparing EDA through catalytic amination of monoethylene glycol (MEG).

In addition to these, the inaugural thesis "Heterogeneous Transition Metal Catalyzed Amination of Aliphatic Diols" from Achim Fischer, Diss. ETH No 12978, 1998, discusses zeolite catalyzed processes for the conversion of monoethyleneglycol and monoethanolamine to ethylenediamine, respectively. WO 2009/083580 A1 relates to a process for the production of ethylene amines from the amination of ethylene oxide, ethylene glycol, or ethanolamine using a sulfonated tetrafluoroethylene based fluoropolymer-copolymer (Nafion) as a catalyst. U.S. Pat. No. 4,918,233 concerns the production of ethylenediamine from monoethanolamine and ammonia with the use of a dealuminated Mordenite catalyst. It is noted that all of the aforementioned processes concern amination processes which are conducted in the liquid phase and require the use of high pressure. Finally, CN 101215239 A concerns the joint preparation of ethylene diamine and aminoethyl piperazine, wherein the process involves the use of a phosphorous modified mordenite catalyst.

Despite the available methods for the amination of monoethanolamine, there remains a need for the provision of improved processes for the preparation of ethylenediamine and/or linear polyethylenimines starting from simpler starting materials.

U.S. Pat. No. 4,939,301 and Feng, R. et al. in Catalysis Communications 2010, Volume 11, Issue 15, pages 1220-1223 respectively report on the amination of ethylene oxide in the liquid phase mainly to monoethanolamine as well as to diethanol- and triethanolamine. In the liquid phase reactions, the formation of diethanolamine and triethanolamine may, however, not be avoided. Furthermore, very high pressures are required for the liquid phase reaction, thus requiring special safety measures and costly apparatus.

U.S. Pat. No. 8,309,771 B2, on the other hand, describes a gas-phase process for the manufacture of ethylene glycol from ethylene oxide.

DD 298 636 A5 discloses synthesis of ethylenediamine by reacting ethylene oxide and ammonia in the gas phase together with a catalyst with crystalline silicate of pentasil type.

DETAILED DESCRIPTION

It was therefore the object of the present invention to provide an improved process for the production of monoethanolamine and of ethylenediamine, as well as linear ethyleneamines. Thus, it has surprisingly been found that starting from ethylene oxide and ammonia as the educts, ethylenediamine as well as monoethanolamine may effectively be generated as the products when conducting the conversion in the gas phase over a zeolite catalyst. In particular, it has quite unexpectedly been found that in the gas phase, a zeolite catalyst may allow for a highly selective reaction of ethylene oxide with ammonia to monoethanolamine and ethylenediamine at high conversion rates, thus allowing for a comparatively facile and highly efficient process for their production from simple starting materials.

Therefore, the present invention relates to a process for the conversion of ethylene oxide to 2-aminoethanol and/or ethane-1,2-diamine and/or linear polyethylenimines of the formula $H_2N-[CH_2CH_2NH]_n-CH_2CH_2NH_2$ wherein n≥1 comprising (i) providing a catalyst comprising a zeolitic material comprising $YO_2$ and $X_2O_3$, wherein Y is a tetravalent element and X is a trivalent element, (ii) providing a gas stream comprising ethylene oxide and ammonia, and (iii) contacting the catalyst provided in (i) with the gas stream provided in (ii) for converting ethylene oxide to 2-aminoethanol and/or ethane-1,2-diamine and/or linear polyethylenimines, wherein n is preferably in the range of from 1 to 8, more preferably of from 1 to 5, more preferably of from 1 to 4, more preferably of from 1 to 3, more preferably of from 1 to 2, wherein more preferably n=1.

Concerning the zeolitic material as such which is contained in (i) the inventive process, no restrictions apply according to the present invention such that any conceivable zeolitic material may be contained therein.

Furthermore, as regards the framework structure of the zeolitic material in (i), again no particular restrictions apply such that the zeolitic material may have any framework structure. Generally, it is conceivable that the framework structure of the zeolitic material is one of ABW, ACO, AEI, AEL, AEN, AET, AFG, AFI, AFN, AFO, AFR, AFS, AFT, AFV, AFX, AFY, AHT, ANA, APC, APD, AST, ASV, ATN, ATO, ATS, ATT, ATV, AVL, AWO, AWW, BCT, BEA, BEC, BIK, BOF, BOG, BOZ, BPH, BRE, BSV, CAN, CAS, CDO, CFI, CGF, CGS, CHA, —CHI, —CLO, CON, CSV, CZP, DAC, DDR, DFO, DFT, DOH, DON, EAB, EDI, EEI, EMT, EON, EPI, ERI, ESV, ETR, EUO, *-EWT, EZT, FAR, FAU, FER, FRA, GIS, GIU, GME, GON, GOO, HEU, IFO, IFR, —IFU, IFW, IFY, IHW, IMF, IRN, IRR, —IRY, ISV, ITE, ITG, ITH, *—ITN, ITR, ITT, —ITV, ITW, IWR, IWS, IWV, IWW, JBW, JNT, JOZ, JRY, JSN, JSR, JST, JSW, KFI, LAU, LEV, LIO, -LIT, LOS, LOV, LTA, LTF, LTJ, LTL, LTN, MAR, MAZ, MEI, MEL, MEP, MER, MFI, MFS, MON, MOR, MOZ, *MRE, MSE, MSO, MTF, MTN, MTT, MTW, MVY, MWF, MWW, NAB, NAT, NES, NON, NPO, NPT, NSI, OBW, OFF, OKO, OSI, OSO, OWE, —PAR, PAU, PCR, PHI, PON, POS, PSI, PUN, RHO, —RON, RRO, RSN, RTE, RTH, RUT, RWR, RWY, SAF, SAO, SAS, SAT, SAV, SBE, SBN, SBS, SBT, SEW, SFE, SFF, SFG, SFH, SFN, SFO, SFS, *SFV, SFW, SGT, SIV, SOD, SOF, SOS, SSF, *—SSO, SSY, STF, STI, *STO, STT, STW, —SVR, SVV, SZR, TER, THO, TOL, TON, TSC, TUN, UEI, UFI, UOS, UOV, UOZ, USI, UTL, UWY, VET, VFI, VNI, VSV, WEI, —WEN, YUG, ZON, including mixtures of two or more thereof. According to the present invention, it is however preferred that the zeolitic material in (i) is selected from the group consisting of zeolitic materials having the MOR, MFI, MEL, FAU, CHA and/or GME framework structure, including combinations of two or more thereof, wherein preferably the zeolitic material comprises one or more zeolites having the MOR and/or MFI framework structure, wherein more preferably the zeolitic material comprises one or more zeolites having the MOR framework structure, wherein more preferably the zeolitic material has the MOR and/or MFI framework structure, wherein more preferably the zeolitic material has the MOR framework structure. Further, it is preferred that the zeolitic material is in its calcined state, wherein, unless specified otherwise, the zeolitic material has been calcined in air for 5 h at 500° C.

As regards the gas stream provided in (ii), no restrictions apply with respect to the amount of ethylene oxide comprised therein such that any conceivable amount of ethylene oxide may be chosen for conducting the inventive process. It is preferred that the gas stream provided in (ii) contains ethylene oxide in an amount in the range of from 0.05 to 10 vol.-%, preferably from 0.1 to 5 vol.-%, more preferably from 0.3 to 2.5 vol.-%, more preferably from 0.5 to 2 vol.-%, more preferably from 0.6 to 1.7 vol.-%, more preferably from 0.7 to 1.5 vol.-%, more preferably from 0.8 to 1.3 vol.-%, and more preferably from 0.9 to 1.1 vol.-%.

As regards the gas stream provided in (ii), again no restrictions apply with respect to the amount of ammonia comprised therein such that any conceivable amount of ammonia may be chosen for conducting the inventive process. It is preferred that the gas stream provided in (ii) contains ammonia in an amount in the range of from 5 to 90 vol.-%, preferably from 10 to 80 vol.-%, more preferably from 20 to 70 vol.-%, more preferably from 25 to 60 vol.-%, more preferably from 30 to 50 vol.-%, more preferably from 35 to 45 vol.-%, more preferably from 37 to 43 vol.-%, and more preferably from 39 to 41 vol.-%.

Therefore, the present invention preferably relates to a process comprising (i) providing a catalyst comprising a zeolitic material comprising $YO_2$ and $X_2O_3$, wherein Y is a tetravalent element and X is a trivalent element, wherein the zeolitic material has the MOR, MFI, MEL, FAU, CHA or GME framework structure, preferably the MOR or MFI framework structure, more preferably the MOR framework structure, (ii) providing a gas stream comprising ethylene oxide in an amount in the range of from 0.05 to 10 vol.-%, preferably from 0.1 to 5 vol.-%, more preferably from 0.3 to 2.5 vol.-%, more preferably from 0.5 to 2 vol.-%, more preferably from 0.6 to 1.7 vol.-%, more preferably from 0.7 to 1.5 vol.-%, more preferably from 0.8 to 1.3 vol.-%, and more preferably from 0.9 to 1.1 vol.-% and ammonia in an amount in the range of from 5 to 90 vol.-%, preferably from 10 to 80 vol.-%, more preferably from 20 to 70 vol.-%, more preferably from 25 to 60 vol.-%, more preferably from 30 to 50 vol.-%, more preferably from 35 to 45 vol.-%, more preferably from 37 to 43 vol.-%, and more preferably from 39 to 41 vol.-%, and (iii) contacting the catalyst provided in (i) with the gas stream provided in (ii) for converting ethylene oxide to 2-aminoethanol and/or ethane-1,2-diamine and/or linear polyethylenimines, wherein n is preferably in the range of from 1 to 8, more preferably of from 1 to 5, more preferably of from 1 to 4, more preferably of from 1 to 3, more preferably of from 1 to 2, wherein more preferably n=1.

As regards the gas stream provided in (ii), no restriction applies as to the molar ratio of ethylene oxide to ammonia. It is preferred that the ammonia:ethylene oxide molar ratio in the gas stream provided in (ii) is in the range of from 5 to 70, preferably of from 10 to 60, more preferably of from 20 to 55, more preferably of from 25 to 50, more preferably of from 30 to 48, more preferably of from 35 to 45, and more preferably of from 38 to 42.

As regards the gas stream provided in (ii), said gas stream may contain one or more further gases. There is no restriction as to the one or more further gases such that any compound or element of the periodic table of elements may be contained in the gas stream as long as it is in its gaseous condition.

As one alternative, the gas stream provided in (ii) further comprises hydrogen, preferably in an amount in the range of from 0.1 to 70 vol.-%, more preferably of from 0.5 to 50 vol.-%, more preferably of from 1 to 40 vol.-%, more preferably of from 5 to 35 vol.-%, more preferably of from 10 to 30 vol.-%, more preferably of from 15 to 25 vol.-%, more preferably of from 17 to 23 vol.-%, and more preferably of from 19 to 21 vol.-%.

As a second alternative, the gas stream provided in (ii) comprises 1 vol.-% or less of hydrogen, preferably 0.5 vol.-% or less, more preferably 0.1 vol.-% or less, more preferably 0.05 vol.-% or less, more preferably 0.001 vol.-% or less, more preferably 0.0005 vol.-% or less, and more preferably 0.0001 vol.-% or less of hydrogen.

Furthermore, the gas stream provided in (ii) may further contain an inert gas, preferably in an amount in the range of from 5 to 90 vol.-%, more preferably of from 10 to 80 vol.-%, more preferably of from 20 to 70 vol.-%, more preferably of from 25 to 60 vol.-%, more preferably of from 30 to 50 vol.-%, more preferably of from 35 to 45 vol.-%, more preferably of from 37 to 43 vol.-%, and more preferably of from 39 to 41 vol.-%. With regard to the inert gas as such, no restriction applies such that any gas may be comprised in said gas stream as long as it is inert with respect to the conversion of ethylene oxide to 2-aminoethanol and/or ethane-1,2-diamine and/or linear polyethylenimines of the formula $H_2N$—$[CH_2CH_2NH]_n$—$CH_2CH_2NH_2$ wherein n≥1. It is preferred that the inert gas comprises one or more gases selected from the group consisting of noble gases, $N_2$, and mixtures of two or more thereof, more preferably from the group consisting of He, Ne, Ar, $N_2$ and mixtures of two or more thereof, wherein more preferably the inert gas comprises Ar and/or $N_2$, preferably $N_2$, and wherein more preferably the inert gas is Ar and/or $N_2$, preferably $N_2$.

Furthermore, the gas stream provided in (ii) may contain $H_2O$. There is in principle no restriction as to the content of water in the gas stream provided in (ii). It is preferred that the gas stream provided in (ii) contains water in an amount of 5 vol.-% or less, more preferably of 3 vol.-% or less, more preferably of 1 vol.-% or less, more preferably of 0.5 vol.-% or less, more preferably of 0.1 vol.-% or less, more preferably of 0.05 vol.-% or less, more preferably of 0.01 vol.-% or less, more preferably of 0.005 vol.-% or less, more preferably of 0.001 vol.-% or less, more preferably of 0.0005 vol.-% or less, and more preferably of 0.0001 vol.-% or less.

According to the present invention, the gas stream provided in (ii) is preferably heated prior to contacting with the catalyst in (iii). As regards the temperature of the gas stream provided in (ii) prior to contacting with the catalyst in (iii) any suitable temperature may be chosen in principle. Thus, the gas stream provided in (ii) is preferably heated to a temperature in the range of from 250 to 600° C., prior to contacting with the catalyst in (iii) at that temperature, preferably in the range of from 260 to 550° C., more preferably from 260 to 500° C., more preferably from 270 to 450° C., more preferably from 270 to 400° C., more preferably from 280 to 370° C., more preferably from 280 to 350° C., more preferably from 290 to 320° C., and more preferably from 290 to 310° C.

According to the present invention, there is in principle no restriction as to the conditions for contacting the catalyst with the gas stream in (iii) provided that the conversion 2-aminoethanol to ethane-1,2-diamine and/or linear polyethylenimines takes place. As regards the contacting of the catalyst with the gas stream in (iii) any suitable pressure may be applied in principle. Thus, it is preferred that the contacting of the gas stream with the catalyst in (iii) is effected at a pressure in the range of from 0.05 to 20 MPa, more preferably from 0.1 to 10 MPa, more preferably from 0.3 to 5 MPa, more preferably from 0.5 to 3 MPa, more preferably from 0.6 to 2 MPa, more preferably from 0.7 to 1.5 MPa, more preferably from 0.8 to 1.3 MPa, and more preferably from 0.9 to 1.1 MPa.

As regards the gas hourly space velocity (GHSV) for contacting of the catalyst with the gas stream in (iii), no particular restrictions apply such that in principle any conceivable gas hourly space velocity may be chosen for conducting the inventive process, provided that it is comprised in the range of from 100 to 30,000 h–1. It is preferred that the contacting of the catalyst with the gas stream in (iii) is effected at a gas hourly space velocity (GHSV) in the range of from 500 to 20,000 $h^{-1}$, more preferably of from 1,000 to 15,000 $h^{-1}$, more preferably of from 2,000 to 10,000 $h^{-1}$, more preferably of from 3,000 to 8,000 $h^{-1}$, more preferably of from 4,000 to 6,000 $h^{-1}$, more preferably of from 4,500 to 5,500 $h^{-1}$, and more preferably of from 4,800 to 5,200 $h^{-1}$.

As regards the zeolitic material comprising $YO_2$ and $X_2O_3$, there is no restriction as to the molar ratio of $YO_2:X_2O_3$ such that in principle any conceivable $YO_2:X_2O_3$ molar ratio may be chosen for conducting the inventive process. It is preferred that the $YO_2:X_2O_3$ molar ratio is in the range of from 4 to 100, more preferably of from 5 to 70, more preferably of from 6 to 50, more preferably of from 8 to 30, more preferably of from 10 to 20, more preferably of from 12 to 17, more preferably of from 13 to 15, and more preferably of from 13.5 to 14.5.

According to the present invention, the zeolitic material comprises $YO_2$ and $X_2O_3$, wherein Y is a tetravalent element and X is a trivalent element.

As regards the tetravalent element Y of the zeolitic material having the MOR framework structure used in the inventive process, no particular restrictions apply such that in principle any conceivable tetravalent element may be chosen for conducting the inventive process. It is preferred that the zeolitic material comprises a tetravalent element Y which is is selected from the group consisting of Si, Sn, Ti, Zr, Ge, and mixtures of two or more thereof, Y more preferably being Si.

Further, as regards the trivalent element X of the zeolitic material having the MOR framework structure used in the inventive process, no particular restrictions apply such that in principle any conceivable trivalent element may be chosen for conducting the inventive process. It is preferred that X is selected from the group consisting of Al, B, In, Ga, and mixtures of two or more thereof, X more preferably being Al and/or B, and more preferably being Al. Thus, it is particularly preferred that the zeolitic material comprises $YO_2$ and $X_2O_3$, wherein Y is Si and X is Al.

Thus, as regards the zeolitic material it is particularly preferred that it comprises $YO_2$ and $X_2O_3$, wherein Y is Si and X is Al, wherein the molar ratio of $YO_2$ and $X_2O_3$ is in the range of from 4 to 100, more preferably of from 5 to 70, more preferably of from 6 to 50, more preferably of from 8 to 30, more preferably of from 10 to 20, more preferably of from 12 to 17, more preferably of from 13 to 15, and more preferably of from 13.5 to 14.5, wherein the zeolitic material has the MOR, MFI, MEL, FAU, CHA or GME framework structure, preferably the MOR or MFI framework structure, more preferably the MOR framework structure.

According to the present invention, the zeolitic material may comprise any further chemical elements, provided that the elements can establish one or more of the above defined framework type. It is preferred that the zeolitic material is in the H-form and contains protons as extra-framework ions, wherein 0.1 wt.-% or less of the extra-framework ions are metal cations, calculated as the element and based on 100 wt.-% of $YO_2$ contained in the zeolitic material, preferably 0.05 wt.-% or less, more preferably 0.001 wt.-% or less, more preferably 0.0005 wt.-% or less, and more preferably 0.0001 wt.-% or less. However, it is particularly preferred that the framework structure of the zeolitic material comprises Si, Al, O and H, wherein at least 99.0 weight-%, preferably at least 99.5 weight-%, more preferably at least 99.9 weight-% of the framework structure of the zeolitic material consist of Si, Al, O and H.

Within the meaning of the present invention, "extra-framework ions" refer to ions and/or ionic compounds contained in the micropores of the zeolitic material and which compensate the charge of the zeolitic framework, wherein according to a preferred meaning of the present invention, "extra-framework ions" refer to cations and/or cationic compounds contained in the micropores of the zeolitic material and which compensate the charge of the zeolitic framework.

According to the present invention, the zeolitic material may contain one or more metal ions M as extra-framework ions. It is preferred that the one or more metal ions M are selected from the group consisting of alkaline earth metals and/or transition metals, more preferably from the group consisting of metals selected from group 4 and groups 6 to 11 of the Periodic Table of the Elements, preferably from group 4 and groups 8 to 11, wherein more preferably the one or more metal ions M are selected from the group consisting of Mg, Ti, Zr, Cu, Co, Cr, Ni, Fe, Mo, Mn, Ru, Rh, Pd, Ag, Os, Ir, Pt, Au, Sn, Zn, Ca, and mixtures of two or more thereof, more preferably from the group consisting of Zr, Cu, Sn, Zn, Ca, Mg, and mixtures of two or more thereof, more preferably from the group consisting of Zr, Cu, Zn, and mixtures of two or more thereof, wherein more preferably the zeolitic material contains Cu and/or Zr, preferably Cu as extra-framework ions.

In the case where the zeolitic material contains extra-framework ions, there is no restriction as to the amount of the extra-framework ions contained in the zeolitic material such that in principle any conceivable amount of M as extra-framework ions calculated as the element and based on 100 wt-% of $YO_2$ contained in the zeolitic material may be chosen for conducting the inventive process. It is preferred that the zeolitic material contains from 0.5 to 15 wt.-% of M as extra-framework ions calculated as the element and based on 100 wt-% of $YO_2$ contained in the zeolitic material, preferably from 1 to 12 wt.-%, more preferably from 1.3, to 9 wt.-%, more preferably from 1.5 to 7 wt.-%, more preferably from 1.8 to 5 wt.-%, more preferably from 2 to 4.5 wt.-%, more preferably from 2.3 to 4 wt.-%, more preferably from 2.5 to 3.7 wt.-%, more preferably from 2.6 to 3.5 wt.-%, more preferably from 2.7 to 3.3 wt.-%, more preferably from 2.9 to 3.1 wt.-%.

Further, in the case where the zeolitic material contains extra-framework ions, there is no restriction as to the $M:X_2O_3$ molar ratio such that in principle any conceivable $M:X_2O_3$ molar ratio of the zeolitic material may be chosen for conducting the inventive process. It is preferred that the $M:X_2O_3$ molar ratio is in the range of from 0.05 to 2.5, preferably of from 0.1 to 2, more preferably of from 0.2 to 1.8, more preferably of from 0.3 to 1.5, more preferably of from 0.5 to 1.2, more preferably of from 0.7 to 1, more preferably of from 0.75 to 0.95, more preferably of from 0.8 to 0.9.

As regards the zeolitic material, it is preferred that it contains substantially no Na, preferably substantially no Na or K, more preferably substantially no alkali metal, and more preferably substantially no alkali metal or alkaline earth metals.

Within the meaning of the present invention, "substantially" as employed in the present invention with respect to the amount of Na, K, alkali metals or alkaline earth metals contained in the framework of the zeolitic material indicates an amount of 0.1 wt.-% or less of Na, K, alkali metals or alkaline earth metals calculated as the element and based on 100 wt.-% of $YO_2$ contained in the zeolitic material, preferably 0.05 wt.-% or less, more preferably 0.001 wt.-% or less, more preferably 0.0005 wt.-% or less, and even more preferably 0.0001 wt.-% or less thereof.

As mentioned above it is particularly preferred according to the present invention that the zeolitic material has the MOR framework structure. In the case where the zeolitic material has the MOR framework structure the crystallites have characteristic properties such as the average particle size that may be measured for example by X-ray diffraction. In particular, the average particle size along the 002 axis of the crystallites may be measured. As regards the average particle size of the zeolitic material having the MOR framework structure along the 002 axis of the crystallites as determined by powder X-ray diffraction, no particular restrictions generally apply according to the present invention with respect to its determination. According to the present invention, it is however preferred that the values for the average particle size of the zeolitic material having the MOR framework structure along the 002 axis of the crystallites is determined according to the method disclosed in U.S. Pat. No. 7,687,423 B2, in particular as described in col. 8, lines 25-48 of said document. It is, however, further preferred according to the present invention that the values for the average particle size of the zeolitic material having the MOR framework structure along the 002 axis of the crystallites as determined by powder X-ray diffraction is determined according to the method described in the experimental section of the present application, wherein the values are determined based on the X-ray diffraction data by fitting the diffracted peak width using the software TOPAS 4.2, wherein instrumental broadening is considered during the peak fitting using the fundamental parameter approach as described in TOPAS 4.2 Users Manual (Bruker AXS GmbH, Östliche Rheinbrückenstr. 49, 76187 Karlsruhe, Germany) leading to a separation of the instrumental from the sample broadening, the sample contribution being determined using a single Lorentzian profile function as defined in the following equation:

$$\beta = \lambda/(L \cdot \cos \theta)$$

where $\beta$ is the Lorentzian full width at half maximum (FWHM), 80 is the X-ray wavelength of the CuKα radiation used, L is the crystallite size, and $\theta$ is the half the scattering angle of the peak position. According to said preferred method, the crystallite size of the 002 reflection is determined in a refinement of the local data surrounding the 002 reflection, from 21° to 24.2° (2θ), wherein single peaks with varying crystallite sizes model the surrounding reflections, the data being collected in the Bragg-Brentano geometry from 2° to 70° (2θ), using a step size of 0.02° (2θ).

According to the present invention, it is preferred that the average particle size of the zeolitic material along the 002 axis of the crystallites as determined by powder X-ray diffraction is in the range of from 5±1 nm to 150±30 nm, more preferably of from 10±1 nm to 100±15 nm, more preferably of from 15±2 nm to 80±12 nm, more preferably of from 20±2 nm to 70±11 nm, more preferably of from 25±3 nm to 65±10 nm, more preferably of from 30±3 nm to 60±9 nm, more preferably of from 35±4 nm to 55±5 nm, and more preferably of from 40±4 nm to 50±5 nm, more preferably of from 44±4 nm to 48±5 nm. It is particularly preferred according to the present invention that the particle size of the zeolitic material along the 002 axis of the crystallites as determined by powder X-ray diffraction is in the range of from 45±5 nm to 47±5 nm. As regards the values of the average particle size of the primary crystallites of the zeolitic material along the 002 axis of the crystallites as determined by powder X-ray diffraction, it is noted that according to the present invention said values are to be understood as containing the following deviation depending on the dimension of the primary crystallites along the 002 axis, said deviation being indicated with "±" following the given value:

>100-200 nm: 20% (e.g. ±30 nm for 150 nm)
>50-100 nm: 15% (e.g. ±15 nm for 100 nm)
>5-50 nm: 10% (e.g. ±5 nm for 50 nm)
2-5 nm: 20% (e.g. ±1 nm for 5 nm)

As regards the average particle size of the primary crystallites of the zeolitic material having the MOR framework structure as determined by powder X-ray diffraction, no particular restrictions apply according to the present invention with respect to its determination. According to the present invention, it is however preferred that the values for the average particle size of the primary crystallites of the zeolitic material having the MOR framework structure as determined by powder X-ray diffraction is determined according to the Scherrer equation. It is, however, further preferred according to the present invention that the values for the average particle size of the primary crystallites of the zeolitic material having the MOR framework structure as determined by powder X-ray diffraction is determined according to the method described in the experimental section of the present application, wherein the values are determined based on the X-ray diffraction data by fitting the diffracted peak width using the software TOPAS 4.2, wherein instrumental broadening is considered during the peak fitting using the fundamental parameter approach as described in TOPAS 4.2 Users Manual (Bruker AXS GmbH, Östliche Rheinbrückenstr. 49, 76187 Karlsruhe, Germany) leading to a separation of the instrumental from the sample broadening, the sample contribution being determined using a single Lorentzian profile function as defined in the following equation:

$$\beta = \lambda/(L \cdot \cos\theta)$$

where $\beta$ is the Lorentzian full width at half maximum (FWHM), $\lambda$ is the X-ray wavelength of the CuK$\alpha$ radiation used, L is the average particle size of the primary crystallites, and $\theta$ is the half the scattering angle of the peak position, the data being collected in the Bragg-Brentano geometry from 2° to 70° (2$\theta$), using a step size of 0.02° (2$\theta$).

It is preferred according to the present invention that the average particle size of the primary crystallites of the zeolitic material as determined by powder X-ray diffraction is in the range of from 5±1 nm to 100±15 nm, preferably the average particle size of the primary crystallites is in the range of from 10±1 nm to 90±14 nm, more preferably from 20±2 nm to 85±13 nm, more preferably from 30±3 nm to 80±12 nm, more preferably from 35±4 nm to 75±11 nm, more preferably from 40±4 nm to 70±11 nm, more preferably from 45±5 nm to 65±10 nm, more preferably from 50±5 nm to 65±10 nm. It is particularly preferred according to the present invention that the average particle size of the primary crystallites of the zeolitic material as determined by powder X-ray diffraction is in the range of from 55±8 nm to 65±10 nm. As regards the values of the average particle size of the primary crystallites of the zeolitic material as determined by powder X-ray diffraction, it is noted that according to the present invention said values are to be understood as containing the following deviations depending on the dimension of the primary crystallites, said deviation being indicated with "±" following the given value:
>100-200 nm: 20% (e.g. ±30 nm for 150 nm)
>50-100 nm: 15% (e.g. ±15 nm for 100 nm)
>5-50 nm: 10% (e.g. ±5 nm for 50 nm)
2-5 nm: 20% (e.g. ±1 nm for 5 nm)

As mentioned above, it is particularly preferred that the catalyst provided in (i) comprises a zeolitic material having the MOR framework structure. It is preferred according to the present invention that the zeolitic material having the MOR framework structure comprises one or more zeolites selected from the group consisting of Mordenite, UZM-14, [Ga—Si—O]-MOR, Ca-Q, LZ-211, Maricopaite, Na-D, RMA-1, and mixtures of two or more thereof, wherein preferably the zeolitic material is UZM-14 and/or Mordenite, preferably Mordenite.

Therefore, as regards the zeolitic material it is particularly preferred that the zeolitic material comprises $YO_2$ and $X_2O_3$, wherein Y is Si and X is Al, wherein the molar ratio of $YO_2$ and $X_2O_3$ is in the range of from 4 to 100, more preferably of from 5 to 70, more preferably of from 6 to 50, more preferably of from 8 to 30, more preferably of from 10 to 20, more preferably of from 12 to 17, more preferably of from 13 to 15, and more preferably of from 13.5 to 14.5, wherein the zeolitic material has the MOR framework structure, and wherein the zeolitic material comprises one or more zeolites selected from the group consisting of Mordenite, UZM-14, [Ga—Si—O]-MOR, Ca-Q, LZ-211, Maricopaite, Na-D, RMA-1, and mixtures of two or more thereof, wherein preferably the zeolitic material is UZM-14 and/or Mordenite, preferably Mordenite.

Further, as regards the zeolitic material comprised in the catalyst provided in (i), the zeolitic material may have the MFI framework structure. Thus, it is preferred that the catalyst provided in (i) comprises a zeolitic material having the MFI framework structure, wherein the zeolitic material having the MFI framework structure preferably comprises one or more zeolites selected from the group consisting of Silicalite, ZSM-5, [Fe—Si—O]-MFI, Monoclinic H-ZSM-5, [Ga—Si—O]-MFI, [As—Si—O]-MFI, AMS-1B, AZ-1, Bor-C, Encilite, Boralite C, FZ-1, LZ-105, Mutinaite, NU-4, NU-5, TS-1, TSZ, TSZ-III, TZ-01, USC-4, USI-108, ZBH, ZKQ-1B, ZMQ-TB, organic-free ZSM-5, and mixtures of two or more thereof, more preferably from the group consisting of ZSM-5, AMS-1 B, AZ-1, FZ-1, LZ-105, NU-4, NU-5, TSZ, TSZ-III, TZ-01, USC-4, USI-108, ZBH, ZKQ-1B, ZMQ-TB, and mixtures of two or more thereof, wherein more preferably the zeolitic material is ZSM-5.

According to the present invention, the catalyst provided in (i) may comprise a zeolitic material comprising $YO_2$ and X203, wherein Y is Si and X is Al, wherein the molar ratio of $YO_2$ and $X_2O_3$ is in the range of from 4 to 100, more preferably of from 5 to 70, more preferably of from 6 to 50, more preferably of from 8 to 30, more preferably of from 10 to 20, more preferably of from 12 to 17, more preferably of from 13 to 15, and more preferably of from 13.5 to 14.5, wherein the zeolitic material has the MFI framework structure, and wherein the zeolitic material comprises one or more zeolites selected from the group consisting of Silicalite, ZSM-5, [Fe—Si—O]-MFI, Monoclinic H-ZSM-5, [Ga—Si—O]-MFI, [As—Si—O]-MFI, AMS-1B, AZ-1, Bor-C, Encilite, Boralite C, FZ-1, LZ-105, Mutinaite, NU-4, NU-5, TS-1, TSZ, TSZ-III, TZ-01, USC-4, USI-108, ZBH, ZKQ-1B, ZMQ-TB, organic-free ZSM-5, and mixtures of two or more thereof, more preferably from the group consisting of ZSM-5, AMS-1B, AZ-1, FZ-1, LZ-105, NU-4, NU-5, TSZ, TSZ-III, TZ-01, USC-4, USI-108, ZBH, ZKQ-1B, ZMQ-TB, and mixtures of two or more thereof, wherein more preferably the zeolitic material is ZSM-5.

Furthermore, the catalyst provided in (i) may further comprise one or more metal oxides and/or one or more metalloid oxides in addition to the zeolitic material. As regards the one or more metal oxides and/or one or more metalloid oxides, no particular restrictions apply such that any conceivable metal oxides and/or metalloid oxides may be chosen for the inventive process. It is preferred that the catalyst provided in (i) further comprises one or more metal oxides and/or one or more metalloid oxides in addition to the zeolitic material, wherein the one or more metal oxides and/or one or more metalloid oxides are more preferably selected from the group consisting of silica, alumina, titania, zirconia, lanthana, magnesia, and mixtures and/or mixed oxides of two or more thereof, more preferably from the group consisting of silica, alumina, titania, zirconia, magnesia, silica-alumina mixed oxides, silica-titania mixed oxides, silica-zirconia mixed oxides, silica-lanthana mixed oxides, silica-zirconia-lanthana mixed oxides, alumina-titania mixed oxides, alumina-zirconia mixed oxides, alumina-lanthana mixed oxides, alumina-zirconia-lanthana mixed oxides, titania-zirconia mixed oxides, and mixtures and/or mixed oxides of two or more thereof, more preferably from the group consisting of silica, alumina, silica-alumina mixed oxides, silica-zirconia mixed oxides, alumina-zirconia mixed oxides, alumina-zirconia-lanthana mixed oxides, and mixtures of two or more thereof, more preferably from the group consisting of alumina, alumina-zirconia mixed oxides, alumina-zirconia-lanthana mixed oxides, and mixtures of two or more thereof, wherein more preferably the catalyst provided in (i) further comprises silica, alumina, and/or zirconia, preferably alumina and/or zirconia, and more preferably alumina in addition to the zeolitic material.

As regards the zeolitic material, it is preferred according to the present invention that the framework of the zeolitic material comprised in the catalyst provided in (i) contains substantially no phosphorous, wherein preferably the zeolitic material comprised in the catalyst provided in (i) contains substantially no phosphorous, wherein more preferably the catalyst provided in (i) contains substantially no phosphorous. Within the meaning of the present invention, "substantially" as employed in the present invention with respect to the amount of phosphorous contained in the framework of the zeolitic material comprised in the catalyst provided in (i) indicates an amount of 0.1 wt.-% or less of phosphorous calculated as the element and based on 100 wt.-% of $YO_2$ in the zeolitic material, preferably 0.05 wt.-% or less, more preferably 0.001 wt.-% or less, more preferably 0.0005 wt.-% or less, and even more preferably 0.0001 wt.-% or less thereof. Furthermore, within the meaning of the present invention, "substantially" as employed in the present invention with respect to the amount of phosphorous contained in the zeolitic material comprised in the catalyst provided in (i) indicates an amount of 0.1 wt.-% or less of phosphorous calculated as the element and based on 100 wt.-% of $YO_2$ in the zeolitic material, and preferably 0.05 wt.-% or less, more preferably 0.001 wt.-% or less, more preferably 0.0005 wt.-% or less, and even more preferably 0.0001 wt.-% or less thereof. Within the meaning of the present invention, the definition of phosphorous substantially not being contained in the framework of the zeolitic material comprised in the catalyst provided in (i) and preferably not being contained in the zeolitic material comprised in the catalyst provided in (i) comprises both elemental phosphorous as well as phosphorous containing compounds.

Further, the zeolitic material may be treated prior to contacting in (iii) of the catalyst provided in (i) with the gas stream provided in (ii), in particular in order to remove $X_2O_3$ at least partially, particularly completely, from its framework structure. However, it is preferred according to the present invention that the zeolitic material is not treated prior to contacting in (iii) of the catalyst provided in (i) with the gas stream provided in (ii). Thus, it is particularly preferred that the zeolitic material having the MOR framework structure has at no point prior to the contacting in (iii) of the catalyst provided in (i) with the gas stream provided in (ii) has the zeolitic material having the MOR framework structure been subject to a treatment for the removal of $X_2O_3$ from its framework structure, and preferably to a treatment for the removal of $X_2O_3$ from the zeolitic material.

As mentioned above, it is particularly preferred that the zeolitic material has the MOR framework structure. As regards the preparation of the zeolitic material having the MOR framework structure used in the inventive process, no particular restrictions apply such that in principle any conceivable zeolitic material having the MOR framework structure may be chosen for conducting the inventive process. It is, however, preferred according to the present invention that the zeolitic material having the MOR framework structure is prepared by a process comprising (1) preparing a mixture comprising at least one source of $YO_2$, at least one source of $X_2O_3$, and comprising one or more organotemplates as structure directing agent;

(2) crystallizing the mixture prepared in (i) for obtaining a zeolitic material having the MOR framework structure;

(3) optionally isolating the zeolitic material obtained in (2);

(4) optionally washing the zeolitic material obtained in (2) or (3);

(5) optionally drying and/or calcining the zeolitic material obtained in (2), (3), or (4);

(6) optionally subjecting the zeolitic material obtained in (2), (3), (4), or (5) to an ion-exchange procedure, wherein extra-framework ions contained in the zeolitic material are ion-exchanged against $H^+$;

(7) optionally subjecting the zeolitic material obtained in (2), (3), (4), (5), or (6) to an ion-exchange procedure, wherein extra-framework ions contained in the zeolitic material are ion-exchanged against one or more metal ions M selected from the group consisting of alkaline earth metals and/or transition metals, preferably from the group consisting of metals selected from group 4 and groups 6 to 11 of the Periodic Table of the Elements, more preferably from group 4 and groups 8 to 11, wherein more preferably the one or more metal ions M are selected from the group consisting of Ti, Zr, Cu, Co, Cr, Ni, Fe, Mo, Mn, Ru, Rh, Pd, Ag, Os, Ir, Pt, Au, Sn, Zn, Ca, Mg and mixtures of two or more thereof, more preferably from the group consisting of Zr, Cu, Sn, Zn, Ca, Mg, and mixtures of two or more thereof, more preferably from the group consisting of Zr, Cu, Zn, and mixtures of two or more thereof, wherein more preferably the extra-framework ions contained in the zeolitic material are ion-exchanged against Cu and/or Zr, preferably Cu;

(8) optionally drying and/or calcining the zeolitic material obtained in (7).

Within the meaning of the present invention, the term "organotemplate" as employed in the present application designates any conceivable organic material which is suitable for template-mediated synthesis of a zeolite material, preferably of a zeolite material having a MOR-type framework-structure, and even more preferably which is suitable for the synthesis of UZM-14 and/or Mordenite.

It is preferred according to the present invention that the one or more organotemplates comprised in the mixture prepared in (1) is selected from the group consisting of tetraalkylammonium containing compounds and tetraalkylphosphonium containing compounds, preferably from the group consisting of tetraalkylammonium cation $R^1R^2R^3R^4N^+$-containing compounds and tetraalkylphosphonium cation $R^1R^2R^3R^4P^+$-containing compounds, wherein $R^1$, $R^2$, $R^3$, and $R^4$ independently from one another stand for optionally substituted and/or optionally branched $(C_1$-$C_6)$ alkyl, preferably $(C_1$-$C_5)$alkyl, more preferably $(C_1$-$C_4)$alkyl, more preferably $(C_1$-$C_3)$alkyl, and even more preferably for optionally substituted methyl or ethyl, wherein even more preferably $R^1$, $R^2$, $R^3$, and $R^4$ stand for optionally substituted ethyl, preferably for unsubstituted ethyl.

It is further preferred that the one or more tetraalkylammonium cation $R^1R^2R^3R^4N^+$-containing compounds and/or that the one or more tetraalkylphosphonium cation $R^1R^2R^3R^4P^+$-containing compounds are salts, preferably one or more salts selected from the group consisting of halides, preferably chloride and/or bromide, more preferably chloride, hydroxide, sulfate, nitrate, phosphate, acetate, and mixtures of two or more thereof, more preferably from the group consisting of chloride, hydroxide, sulfate, and mixtures of two or more thereof, more preferably the one or more tetraalkylammonium cation $R^1R^2R^3R^4N^+$-containing compounds and/or the one or more tetraalkylphosphonium cation $R^1R^2R^3R^4P^+$-containing compounds are hydroxides and/or bromides, and even more preferably bromides.

It is preferred according to the present invention that the one or more organotemplates comprised in the mixture prepared in (1) is selected from the group consisting of N,N,N,N-tetra($C_1$-$C_4$) alkylammonium and N,N,N,N-tetra ($C_1$-$C_4$)alkylphosphonium compounds, preferably from the group consisting of N,N,N,N-tetra($C_1$-$C_3$)alkylammonium and N,N,N,N-tetra($C_1$-$C_3$) alkylphosphonium compounds, more preferably from the group consisting of N,N,N,N-tetra ($C_1$-$C_2$)alkylammonium and N,N,N,N-tetra($C_1$-$C_2$)alkylphosphonium compounds, more preferably from the group consisting of N,N,N,N-tetra($C_1$-$C_2$)alkylammonium and N,N,N,N-tetra($C_1$-$C_2$) alkylphosphonium compounds, more preferably from the group consisting of N,N,N,N-tetraethylammonium compounds, N,N,N,N-tetramethylammonium compounds, N,N,N,N-tetraethylphosphonium compounds, N,N,N,N-tetramethylphosphonium compounds, and mixtures of two or more thereof. It is particularly preferred according to the present invention that the one or more organotemplates comprise one or more N,N,N,N-tetraethylammonium or N,N,N,N-tetraethylphosphonium compounds, preferably one or more N,N,N,N-tetraethylammonium compounds.

Therefore, it is preferred according to the present invention that one or more of a N,N,N,N-tetraethylammonium halide and a N,N,N,N-tetraethylphosphonium halide is employed as organotemplate in the process for the template-mediated synthesis of a zeolite material having the MOR framework structure. Thus, it is particularly preferred to employ one or more of N,N,N,N-tetraethylammonium chloride, N,N,N,N-tetraethylammonium bromide, N,N,N,N-tetraethylphosphonium chloride, N,N,N,N-tetraethylphosphonium bromide and a mixture of two or more thereof.

As regards the organotemplate: $YO_2$ molar ratio of the one or more organotemplates to $YO_2$ in the mixture provided according to (1) for preparing the zeolitic material having the MOR framework structure, no particular restrictions apply such that in principle any conceivable organotemplate: $YO_2$ molar ratio may be chosen for conducting the process for preparing the zeolitic material having the MOR framework structure. Thus, by way of example, the organotemplate: $YO_2$ molar ratio of the one or more organotemplates to $YO_2$ in the mixture provided according to (1) may range from 0.005 to 0.14, preferably from 0.01 to 0.3, more preferably from 0.02 to 0.2, more preferably from 0.025 to 0.14, more preferably from 0.03 to 0.1, more preferably from 0.035 to 0.08, more preferably from 0.04 to 0.06. It is, however, particularly preferred according to the present invention that the organotemplate: $YO_2$ molar ratio of the one or more organotemplates to $YO_2$ in the mixture provided according to (1) ranges from 0.045 to 0.055.

It is alternatively preferred according to the present invention that the mixture prepared in (1) and crystallized in (2) contains substantially no zeolitic material. Further, it is preferred that the mixture prepared in (1) and crystallized in (2) contains substantially no seed crystals. Within the meaning of the present invention wherein the mixture prepared in (1) and crystallized in (2) contains substantially no zeolitic material and preferably contains substantially no seed crystals, this indicates that the mixture prepared in (1) and crystallized in (2) may only contain zeolitic material and preferably may only contain seed crystals in an amount of 0.1 wt.-% or less based on 100 wt.-% of $YO_2$ contained in the mixture, and preferably in an amount of 0.05 wt.-% or less, more preferably of 0.001 wt.-% or less, more preferably of 0.0005 wt.-% or less, and even more preferably in an amount of 0.0001 wt.-% or less based on 100 wt.-% of $YO_2$ contained in the mixture. Said amounts of zeolitic material and preferably of seed crystals, if at all present in the mixture prepared in (1) and crystallized in (2), may also be denoted as "impurities" or "trace amounts" within the meaning of the present invention.

It is preferred that in (6) of the process for preparing the zeolitic material having the MOR framework structure used in the inventive process the step of subjecting the zeolitic material to an ion-exchange procedure includes the steps of (6.a) subjecting the zeolitic material obtained in (2), (3), (4), or (5) to an ion-exchange procedure, wherein extra-framework ions contained in the zeolitic material are ion-exchanged against $NH_4^+$;

(6.b) calcining the ion-exchanged zeolitic material obtained in (6.a) for obtaining the H-form of the zeolitic material.

As regards calcining in (5), (6.b), (8) and/or (12), no particular restrictions apply such that in principle any conceivable temperature and/or duration may be chosen for conducting the process for preparing the zeolitic material having the MOR framework structure. Thus, by way of example, calcining in (5), (6.b), (8) and/or (12) may be conducted at a temperature in the range of from 200 to 850° C., preferably of from 250 to 800° C., more preferably of from 300 to 750° C., more preferably of from 350 to 700° C., more preferably of from 400 to 650° C., more preferably of from 450 to 620° C., more preferably of from 500 to 600° C., and more preferably of from 520 to 580° C. It is, however, particularly preferred according to the present invention that calcining in (5), (6.b), (8) and/or (12) is conducted at a temperature in the range of from 540 to 560° C.

Further, by way of example, calcining of the zeolitic material in (5), (6.b), (8) and/or (12) may be effected in batch mode, in semi-continuous mode, or in continuous mode. Calcination in (6.b) is performed by heating of the zeolitic material to a temperature according to any of the particular and performed embodiments defined in the present application and holding it at that temperature for a duration ranging from 0.5 to 36 h, preferably from 1 to 32 h, more preferably from 2 to 28 h, more preferably from 4 to 24 h, more preferably from 6 to 20 h, more preferably from 8 to 18 h, and more preferably from 10 to 14 h. It is, however, particularly preferred according to the present invention that calcining of the zeolitic material in (5), (6.b), (8) and/or (12) is effected by heating of the zeolitic material to a given temperature and holding it at that temperature for a duration ranging from 11.5 to 12.5 h. Furthermore, it is particularly preferred according to the present invention that calcining in (5), (6.b), (8) and/or (12) is conducted at a temperature in the range of from 540 to 560° C. for a duration ranging from 11.5 to 12.5 h. When conducted in semi-continuous or in continuous mode, the duration of calcination corresponds to the residence time of the zeolitic material in the given calciner operating in a semi-continuous mode or in continuous mode.

In case the process is carried out in a larger scale, it is preferred to perform the calcination in semi-continuous mode or in continuous mode, more preferably in continuous mode. Even more preferably, calcining the zeolitic material in (5), (6.b), (8) and/or (12) is carried out in continuous mode with a rate in the range of from 0.2 to 50.0 kg of the zeolitic material per hour, preferably from 0.5 to 2.0 kg of the zeolitic material per hour. Conceivable apparatuses which can be used for such a preferred continuous calcination include, for example, a band calciner and/or a rotary calciner, wherein preferably a rotary calciner is used.

According to the present invention, it is however particularly preferred that, if the zeolitic material obtained in (7) which is ion-exchanged with one or more metal ions M is subject to a heating treatment such as drying and/or calcination, said treatment does not involve a temperature of 540° C. or greater, and preferably does not involve a temperature of 520° C. or greater, more preferably of 500° C. or greater, more preferably of 450° C. or greater, more preferably of 400° C. or greater, more preferably of 350° C. or greater, more preferably of 300° C. or greater, more preferably of 250° C. or greater, and more preferably of 200° C. According to the present invention it is particularly preferred that zeolitic material obtained in (7) which is ion-exchanged with one or more metal ions M is not subject to a temperature of 150° C. or greater. Thus, according to said particularly preferred embodiments, the zeolitic material obtained in (7) which is ion-exchanged with one or more metal ions M is not subject to calcination according to (8) as defined in any of the particular and preferred embodiments of the present application.

It is preferred according to the present invention that in (7) the zeolitic material is ion-exchanged such as to obtain a loading of the one or more metal ions M in the zeolitic material ranging from 0.5 to 15 wt.-% calculated as the one or more elements M and based on 100 wt.-% of $YO_2$ contained in the zeolitic material, preferably from 1 to 12 wt.-%, more preferably from 1.3 to 9 wt.-%, more preferably from 1.5 to 7 wt.-%, more preferably from 1.8 to 5 wt.-%, more preferably from 2 to 4.5 wt.-%, more preferably from 2.3 to 4 wt.-%, more preferably from 2.5 to 3.7 wt.-%, more preferably from 2.6 to 3.5 wt.-%, more preferably from 2.7 to 3.3 wt.-%. It is particularly preferred according to the present invention that in (7) the zeolitic material is ion-exchanged such as to obtain a loading of the one or more metal ions M in the zeolitic material ranging from 2.9 to 3.1 wt.-%.

As regards the element Y used for preparing the zeolitic material having the MOR framework structure, no particular restrictions apply such that in principle any conceivable tetravalent element may be chosen for conducting the process for preparing the zeolitic material having the MOR framework structure. Thus, it is preferred that Y is selected from the group consisting of Si, Sn, Ti, Zr, Ge, and combinations of two or more thereof. It is, however, particularly preferred according to present invention that Y is Si.

It is preferred according to the present invention that the at least one source for $YO_2$ comprises one or more compounds selected from the group consisting of silicas, silicates, and mixtures thereof, preferably from the group consisting of fumed silica, silica hydrosols, reactive amorphous solid silicas, silica gel, silicic acid, water glass, sodium metasilicate hydrate, sesquisilicate, disilicate, colloidal silica, silicic acid esters, tetraalkoxysilanes, and mixtures of two or more thereof, more preferably from the group consisting of fumed silica, silica hydrosols, silica gel, silicic acid, water glass, colloidal silica, silicic acid esters, tetraalkoxysilanes, and mixtures of two or more thereof, more preferably from the group consisting of fumed silica, silica hydrosols, silica gel, colloidal silica, and mixtures of two or more thereof, more preferably from the group consisting of fumed silica, silica gel, colloidal silica, and mixtures of two or more thereof, more preferably the at least one source of $YO_2$ is selected from the group consisting of fumed silica, colloidal silica, and mixtures thereof. It is particularly preferred according to the present invention that fumed silica is employed as the source of $YO_2$.

As regards the element X used for preparing the zeolitic material having the MOR framework structure, no particular restrictions apply such that in principle any conceivable trivalent element may be chosen for conducting the process for preparing the zeolitic material having the MOR framework structure. Thus, by way of example, X may be selected from the group consisting of Al, B, In, Ga, and combinations of two or more thereof. It is, however, particularly preferred according to the present invention that X is Al.

It is preferred according to the present invention the at least one source for $X_2O_3$ comprises one or more aluminum salts, preferably an aluminate of an alkali metal, wherein the alkali metal is preferably selected from the group consisting of Li, Na, K, Rb, and Cs, wherein more preferably the alkali metal is Na and/or K, and wherein even more preferably the alkali metal is Na.

As regards the $YO_2:X_2O_3$ molar ratio of the mixture prepared in (1), no particular restrictions apply such that in principle any conceivable $YO_2:X_2O_3$ molar ratio may be chosen for conducting the process for preparing the zeolitic material having the MOR framework structure used in the inventive process. Thus, by way of example, the $YO_2:X_2O_3$ molar ratio of the mixture prepared in (1) may range from 2 to 50, preferably from 4 to 40, more preferably from 6 to 35, more preferably from 10 to 30, more preferably from 13 to 25, more preferably from 15 to 23, more preferably from 17 to 22. It is particularly preferred according to the present invention that the $YO_2:X_2O_3$ molar ratio of the mixture prepared in (1) ranges from 19 to 21.

According to the present invention, it is preferred that the mixture prepared in (1) further comprises a solvent system containing one or more solvents, wherein the solvent system preferably comprises one or more solvents selected from the group consisting of polar protic solvents and mixtures thereof, preferably from the group consisting of n-butanol, isopropanol, propanol, ethanol, methanol, water, and mixtures thereof, more preferably from the group consisting of ethanol, methanol, water, and mixtures thereof, wherein more preferably the solvent system comprises water. It is particularly preferred according to the present invention that water, preferably deionized water, is used as the solvent system.

According to the present invention, it is further preferred that when the mixture prepared in (1) and crystallized in (2) comprises one or more organotemplates, and when the mixture prepared in (1) comprises water as the solvent system, the $H_2O:YO_2$ molar ratio of the mixture prepared in (1) ranges from 5 to 100, preferably from 10 to 80, more preferably from 20 to 70, more preferably from 25 to 65, more preferably from 30 to 60, more preferably from 35 to 55, more preferably from 37 to 50, more preferably from 39 to 47. It is particularly preferred that when the mixture prepared in (1) and crystallized in (2) comprises one or more organotemplates, and when the mixture prepared in (1) comprises water as the solvent system, the $H_2O:YO_2$ molar ratio of the mixture prepared in (1) ranges from 40 to 45.

According to the present invention, it is preferred that the mixture prepared in (1) further comprises one or more alkali metals (AM), preferably the one or more alkali metals are selected from the group consisting of Li, Na, K, Cs, and mixtures thereof, more preferably the mixture prepared in (1) further comprises Na and/or K, preferably Na as the alkali metal AM.

As regards the AM:YO$_2$ molar ratio of alkali metals to YO$_2$ in the mixture prepared in (1) when the mixture prepared in (1) and crystallized in (2) comprises one or more organotemplates, no particular restrictions apply such that any conceivable AM:YO$_2$ molar ratio may be chosen for the process of preparing the zeolitic material having the MOR framework structure used in the inventive process. Thus, by way of example, when the mixture prepared in (1) and crystallized in (2) comprises one or more organotemplates, the AM:YO$_2$ molar ratio of alkali metals to YO$_2$ in the mixture prepared in (1) may be in the range of from 0.01 to 3, preferably of from 0.05 to 2.5, more preferably of from 0.1 to 2, more preferably of from 0.2 to 1.5, more preferably of from 0.3 to 1.2, more preferably of from 0.35 to 1, more preferably of from 0.4 to 0.9, more preferably of from 0.45 to 0.8, more preferably of from 0.5 to 0.7. It is, however, particularly preferred according to the present invention that the AM:YO$_2$ molar ratio of alkali metals to YO$_2$ in the mixture prepared in (1), when the mixture prepared in (1) and crystallized in (2) comprises one or more organotemplates, ranges from 0.55 to 0.65.

As regards the crystallization in (2), no particular restrictions apply such that in principle any conceivable conditions of crystallization may be chosen for the process of preparing the zeolitic material having the MOR framework structure.

Thus, by way of example, the crystallization in (2) may involve heating of the mixture prepared in (1), preferably to a temperature ranging from 75 to 220° C., more preferably from 90 to 210° C., more preferably from 110 to 205° C., more preferably from 130 to 200° C., more preferably from 140 to 195° C., more preferably from 150 to 190° C., more preferably from 155 to 185° C., more preferably from 160 to 180° C. It is, however, particularly preferred according to the present invention that the crystallization in (2) involves heating of the mixture prepared in (1) to a temperature ranging from 165 to 175° C.

Further, by way of example, the crystallization in (2) may be conducted under autogenous pressure, preferably under solvothermal conditions. It is, however, particularly preferred according to the present invention that the crystallization in (2) is conducted under hydrothermal conditions.

According to the present invention, it is preferred that when the mixture prepared in (1) and crystallized in (2) comprises one or more organotemplates, the crystallization in (2) involves heating of the mixture prepared in (1) for a period in the range of from 50 to 115 h, more preferably from 60 to 95 h, more preferably from 65 to 85 h, more preferably from 70 to 80 h, more preferably from 70 to 78 h, and more preferably from 75 to 77 h.

It is preferred according to the present invention that the zeolitic material having an MOR framework structure crystallized in (2) is Mordenite.

It is preferred according to the present invention that the mixture prepared in (1) and crystallized in (2) contains substantially no phosphorous.

Within the meaning of the present invention, "substantially" as employed in the present invention with respect to the amount of phosphorous contained in the mixture prepared in (1) and crystallized in (2) indicates an amount of 0.1 wt.-% or less of phosphorous calculated as the element and based on 100 wt.-% of YO$_2$ in the mixture, preferably 0.05 wt.-% or less, more preferably 0.001 wt.-% or less, more preferably 0.0005 wt.-% or less, and even more preferably 0.0001 wt.-% or less thereof. Within the meaning of the present invention, the definition of phosphorous substantially not being contained in the mixture prepared in (1) and crystallized in (2) comprises both elemental phosphorous as well as phosphorous containing compounds.

According to the present invention, it is preferred that the framework of the zeolitic material obtained in (2) contains substantially no phosphorous, more preferably the zeolitic material obtained in (2) contains substantially no phosphorous.

Within the meaning of the present invention, "substantially" as employed in the present invention with respect to the amount of phosphorous contained in the framework of the zeolitic material obtained in (2) indicates an amount of 0.1 wt.-% or less of phosphorous calculated as the element and based on 100 wt.-% of YO$_2$ in the zeolitic material, preferably 0.05 wt.-% or less, more preferably 0.001 wt.-% or less, more preferably 0.0005 wt.-% or less, and even more preferably 0.0001 wt.-% or less thereof. Furthermore, within the meaning of the present invention, "substantially" as employed in the present invention with respect to the amount of phosphorous contained in the zeolitic material obtained in (2) indicates an amount of 0.1 wt.-% or less of phosphorous calculated as the element and based on 100 wt.-% of YO$_2$ in the zeolitic material, and preferably 0.05 wt.-% or less, more preferably 0.001 wt.-% or less, more preferably 0.0005 wt.-% or less, and even more preferably 0.0001 wt.-% or less thereof. Within the meaning of the present invention, the definition of phosphorous substantially not being contained in the framework of the zeolitic material obtained in (2) and preferably not being contained in the mixture prepared in (1) and crystallized in (2) comprises both elemental phosphorous as well as phosphorous containing compounds.

Therefore, it is particularly preferred according to the present invention that the zeolitic material having the MOR framework structure is prepared by a process comprising (1) preparing a mixture comprising at least one source of YO$_2$, wherein Y is preferably Si, at least one source of X$_2$O$_3$, wherein X is preferably Al, and comprising one or more of N,N,N,N-tetraethylammonium chloride, N,N,N,N-tetraethylammonium bromide, N,N,N,N-tetraethylphosphonium chloride, N,N,N,N-tetraethylphosphonium bromide and a mixture of two or more thereof as structure directing agent;

(2) crystallizing the mixture prepared in (i) for obtaining a zeolitic material having the MOR framework structure, wherein crystallizing preferably includes heating of the mixture prepared in (1) to a temperature in the range of from 75 to 220° C., wherein crystallizing is preferably conducted under hydrothermal conditions, wherein crystallizing preferably involves heating of the mixture prepared in (1) for a period in the range of from 50 to 115 h;

(3) optionally isolating the zeolitic material obtained in (2);

(4) optionally washing the zeolitic material obtained in (2) or (3);

(5) optionally drying and/or calcining the zeolitic material obtained in (2), (3), or (4);

(6) optionally subjecting the zeolitic material obtained in (2), (3), (4), or (5) to an ion-exchange procedure, wherein extra-framework ions contained in the zeolitic material are ion-exchanged against H$^+$;

(7) optionally subjecting the zeolitic material obtained in (2), (3), (4), (5), or (6) to an ion-exchange procedure, wherein extra-framework ions contained in the zeolitic material are ion-exchanged against one or more metal ions M selected from the group consisting of alkaline earth metals and/or transition metals, preferably from the group consisting of metals selected from group 4 and groups 6 to 11 of the Periodic Table of the Elements, more preferably from group 4 and groups 8 to 11, wherein more preferably the one or more metal ions M are selected from the group consisting of Ti, Zr, Cu, Co, Cr, Ni, Fe, Mo, Mn, Ru, Rh, Pd, Ag, Os, Ir, Pt, Au, Sn, Zn, Ca, Mg and mixtures of two or more thereof, more preferably from the group consisting of Zr, Cu, Sn, Zn, Ca, Mg, and mixtures of two or more thereof, more preferably from the group consisting of Zr, Cu, Zn, and mixtures of two or more thereof, wherein more preferably the extra-framework ions contained in the zeolitic material are ion-exchanged against Cu and/or Zr, preferably Cu;

(8) optionally drying and/or calcining the zeolitic material obtained in (7).

According to the present invention, there is no restriction as to any treatment, in particular by heating, of the zeolitic material obtained in (7). However, it is preferred that the zeolitic material obtained in (7) is not subject to a temperature of 540° C. or greater, more preferably of 520° C. or greater, more preferably of 500° C. or greater, more preferably of 450° C. or greater, more preferably of 400° C. or greater, more preferably of 350° C. or greater, more preferably of 300° C. or greater, more preferably of 250° C. or greater, more preferably of 200° C., and more preferably of 150° C. or greater.

There is no particular restriction according to the present invention as to the form in which the zeolitic material having the MOR framework structure may be provided in the catalyst employed in the inventive process. Thus, the zeolitic material may be used as such, or may be employed together with further components. According to the inventive process it is thus preferred that the zeolitic material is comprised in the catalyst employed in the inventive process in the form of a molding. Accordingly it is preferred according to the present invention that the preferred process for preparing the zeolitic material according to any of the particular preferred embodiments described in the present application further comprises (9) mixing the zeolitic material obtained in (2), (3), (4), (5), (6), (7) or (8) with one or more binders;

(10) kneading of the mixture obtained in (9);

(11) molding of the kneaded mixture obtained in (10) to obtain one or more moldings; and

(12) drying and/or calcining the one or more moldings obtained in (11).

With respect to the one or more binders with which the zeolitic material obtained in (7) or (8) may be mixed, no particular restrictions apply such that in principle any suitable binder may be employed. Thus, by way of example, the one or more binders may be selected from the group consisting of inorganic binders, wherein according to the present invention it is preferred that the one or more binders comprise one or more sources of a metal oxide and/or of a metalloid oxide or one or more sources of graphite, wherein the one or more sources of a metal oxide and/or of a metalloid oxide are preferably selected from the group consisting of silica, alumina, titania, zirconia, lanthana, magnesia, and mixtures and/or mixed oxides of two or more thereof, more preferably from the group consisting of silica, alumina, titania, zirconia, magnesia, silica-alumina mixed oxides, silica-titania mixed oxides, silica-zirconia mixed oxides, silica-lanthana mixed oxides, silica-zirconia-lanthana mixed oxides, alumina-titania mixed oxides, alumina-zirconia mixed oxides, alumina-lanthana mixed oxides, alumina-zirconia-lanthana mixed oxides, titania-zirconia mixed oxides, and mixtures and/or mixed oxides of two or more thereof, more preferably from the group consisting of silica, alumina, silica-alumina mixed oxides, silica-zirconia mixed oxides, alumina-zirconia mixed oxides, alumina-zirconia-lanthana mixed oxides, and mixtures of two or more thereof, more preferably from the group consisting of alumina, alumina-zirconia mixed oxides, alumina-zirconia-lanthana mixed oxides, and mixtures of two or more thereof, wherein more preferably the one or more binders comprise one or more sources of silica, alumina, zirconia, and/or graphite, the one or more binders preferably comprising one or more sources of alumina and/or zirconia, preferably of alumina, wherein more preferably the binder consists of one or more sources of alumina and/or zirconia, preferably of one or more sources of alumina, wherein more preferably the binder comprises alumina and/or zirconia, preferably alumina, wherein more preferably the binder consists of alumina and/or zirconia, preferably of alumina.

According to the present invention, it is preferred that ethylene oxide and/or 2-aminoethanol comprised in the gas stream obtained in (iii) is separated from said gas stream and recycled to (ii).

The present invention is further illustrated by the following set of embodiments and combinations of embodiments resulting from the dependencies and back-references as indicated. In particular, it is noted that in each instance where a range of embodiments is mentioned, for example in the context of a term such as "The process of any one of embodiments 1 to 4", every embodiment in this range is meant to be explicitly disclosed for the skilled person, i.e. the wording of this term is to be understood by the skilled person as being synonymous to "The process of any one of embodiments 1, 2, 3, and 4":

1. A process for the conversion of ethylene oxide to 2-aminoethanol and/or ethane-1,2-diamine and/or linear polyethylenimines of the formula $H_2N-[CH_2CH_2NH]_n-CH_2CH_2NH_2$ wherein $n \geq 1$ comprising (i) providing a catalyst comprising a zeolitic material comprising $YO_2$ and $X_2O_3$, wherein Y is a tetravalent element and X is a trivalent element;

(ii) providing a gas stream comprising ethylene oxide and ammonia;

(iii) contacting the catalyst provided in (i) with the gas stream provided in (ii) for converting ethylene oxide to 2-aminoethanol and/or ethane-1,2-diamine and/or linear polyethylenimines, wherein n preferably is in the range of from 1 to 8, more preferably from 1 to 5, more preferably from 1 to 4, more preferably from 1 to 3, more preferably from 1 to 2, wherein more preferably n=1.

2. The process of embodiment 1, wherein in (i) the zeolitic material is selected from the group consisting of zeolitic materials having the MOR, MFI, MEL, FAU, CHA and/or GME framework structure, including combinations of two or more thereof, wherein preferably the zeolitic material comprises one or more zeolites having the MOR and/or MFI framework structure, wherein more preferably the zeolitic material comprises one or more zeolites having the MOR framework structure, wherein more preferably the zeolitic material has the MOR and/or MFI framework structure, wherein more preferably the zeolitic material has the MOR framework structure.

3. The process of embodiment 1 or 2, wherein the gas stream provided in (ii) and contacted with the catalyst in (iii) contains ethylene oxide in an amount in the range of from 0.05 to 10 vol.-%, preferably from 0.1 to 5 vol.-%, more preferably from 0.3 to 2.5 vol.-%, more preferably from 0.5 to 2 vol.-%, more preferably from 0.6 to 1.7 vol.-%, more preferably from 0.7 to 1.5 vol.-%, more preferably from 0.8 to 1.3 vol.-%, and more preferably from 0.9 to 1.1 vol.-%.

4. The process of any of embodiments 1 to 3, wherein the gas stream provided in (ii) and contacted with the catalyst in (iii) contains ammonia in an amount in the range of from 5 to 90 vol.-%, preferably from 10 to 80 vol.-%, more preferably from 20 to 70 vol.-%, more preferably from 25 to 60 vol.-%, more preferably from 30 to 50 vol.-%, more preferably from 35 to 45 vol.-%, more preferably from 37 to 43 vol.-%, and more preferably from 39 to 41 vol.-%.

5. The process of any of embodiments 1 to 4, wherein the ammonia:ethylene oxide molar ratio in the gas stream provided in (ii) and contacted with the catalyst in (iii) is in the range of from 5 to 70, preferably from 10 to 60, more preferably from 20 to 55, more preferably from 25 50, more preferably from 30 to 48, more preferably from 35 to 45, and more preferably from 38 to 42.

6. The process of any of embodiments 1 to 5, wherein the gas stream provided in (ii) and contacted with the catalyst in (iii) further contains hydrogen in an amount in the range of from 0.1 to 70 vol.-%, preferably from 0.5 to 50 vol.-%, more preferably from 1 to 40 vol.-%, more preferably from 5 to 35 vol.-%, more preferably from 10 to 30 vol.-%, more preferably from 15 to 25 vol.-%, more preferably from 17 to 23 vol.-%, and more preferably from 19 to 21 vol.-%.

7. The process of any of embodiments 1 to 6, wherein the gas stream provided in (ii) and contacted with the catalyst in (iii) contains 1 vol.-% or less of hydrogen, preferably 0.5 vol.-% or less, more preferably 0.1 vol.-% or less, more preferably 0.05 vol.-% or less, more preferably 0.001 vol.-% or less, more preferably 0.0005 vol.-% or less, and more preferably 0.0001 vol.-% or less of hydrogen.

8. The process of any of embodiments 1 to 7, wherein the gas stream provided in (ii) and contacted with the catalyst in (iii) further contains an inert gas in an amount in the range of from 5 to 90 vol.-%, preferably from 10 to 80 vol.-%, more preferably from 20 to 70 vol.-%, more preferably from 25 to 60 vol.-%, more preferably from 30 to 50 vol.-%, more preferably from 35 to 45 vol.-%, more preferably from 37 to 43 vol.-%, and more preferably from 39 to 41 vol.-%.

9. The process of embodiment 8, wherein the inert gas comprises one or more gases selected from the group consisting of noble gases, $N_2$, and mixtures of two or more thereof, preferably from the group consisting of He, Ne, Ar, $N_2$ and mixtures of two or more thereof, wherein more preferably the inert gas comprises Ar and/or $N_2$, preferably $N_2$, and wherein more preferably the inert gas is Ar and/or $N_2$, preferably $N_2$.

10. The process of any of embodiments 1 to 9, wherein the gas stream provided in (ii) and contacted with the catalyst in (iii) contains $H_2O$ in an amount of 5 vol.-% or less, preferably of 3 vol.-% or less, more preferably of 1 vol.-% or less, more preferably of 0.5 vol.-% or less, more preferably of 0.1 vol.-% or less, more preferably of 0.05 vol.-% or less, more preferably of 0.01 vol.-% or less, more preferably of 0.005 vol.-% or less, more preferably of 0.001 vol.-% or less, more preferably of 0.0005 vol.-% or less, and more preferably of 0.0001 vol.-% or less.

11. The process of any of embodiments 1 to 10, wherein the gas stream provided in (ii) is heated to a temperature in the range of from 250 to 600° C., prior to contacting with the catalyst in (iii) at that temperature, preferably in the range of from 260 to 550° C., more preferably from 260 to 500° C., more preferably from 270 to 450° C., more preferably from 270 to 400° C., more preferably from 280 to 370° C., more preferably from 280 to 350° C., more preferably from 290 to 320° C., and more preferably from 290 to 310° C.

12. The process of any of embodiments 1 to 11, wherein the contacting of the catalyst with the gas stream in (iii) is effected at a pressure in the range of from 0.05 to 20 MPa, preferably from 0.1 to 10 MPa, more preferably from 0.3 to 5 MPa, more preferably from 0.5 to 3 MPa, more preferably from 0.6 to 2 MPa, more preferably from 0.7 to 1.5 MPa, more preferably from 0.8 to 1.3 MPa, and more preferably from 0.9 to 1.1 MPa.

13. The process of any of embodiments 1 to 12, wherein the contacting of the catalyst with the gas stream in (iii) is effected at a gas hourly space velocity (GHSV) in the range of from 100 to 30,000 $h^{-1}$, preferably from 500 to 20,000 $h^{-1}$, more preferably from 1,000 to 15,000 $h^{-1}$, more preferably from 2,000 to 10,000 $h^{-1}$, more preferably from 3,000 to 8,000 $h^{-1}$, more preferably from 4,000 to 6,000 $h^{-1}$, more preferably from 4,500 to 5,500 $h^{-1}$, and more preferably from 4,800 to 5,200 $h^{-1}$.

14. The process of any of embodiments 1 to 13, wherein the zeolitic material displays a $YO_2:X_2O_3$ molar ratio in the range of from 4 to 100, preferably from 5 to 70, more preferably from 6 to 50, more preferably from 8 to 30, more preferably from 10 to 20, more preferably from 12 to 17, more preferably from 13 to 15, and more preferably from 13.5 to 14.5.

15. The process of any of embodiments 1 to 14, wherein Y is selected from the group consisting of Si, Sn, Ti, Zr, Ge, and mixtures of two or more thereof, Y preferably being Si.

16. The process of any of embodiments 1 to 15, wherein X is selected from the group consisting of Al, B, In, Ga, and mixtures of two or more thereof, X preferably being Al and/or B, and more preferably being Al.

17. The process of any of embodiments 1 to 16, wherein the zeolitic material is in the H-form and contains protons as extra-framework ions, wherein 0.1 wt.-% or less of the extra-framework ions are metal cations, calculated as the element and based on 100 wt.-% of $YO_2$ contained in the zeolitic material, preferably 0.05 wt.-% or less, more preferably 0.001 wt.-% or less, more preferably 0.0005 wt.-% or less, and more preferably 0.0001 wt.-% or less.

18. The process of any of embodiments 1 to 17, wherein the zeolitic material contains one or more metal ions M as extra-framework ions, wherein the one or more metal ions M are selected from the group consisting of alkaline earth metals and/or transition metals, more preferably from the group consisting of metals selected from group 4 and groups 6 to 11 of the Periodic Table of the Elements, preferably from group 4 and groups 8 to 11, wherein more preferably the one or more metal ions M are selected from the group consisting of Mg, Ti, Zr, Cu, Co, Cr, Ni, Fe, Mo, Mn, Ru, Rh, Pd, Ag, Os, Ir, Pt, Au, Sn, Zn, Ca and mixtures of two or more thereof, more preferably from the group consisting of Zr, Cu, Sn, Zn, Ca, Mg, and mixtures of two or more thereof, more preferably from the group consisting of Zr, Cu, Zn, and mixtures of two or more thereof, wherein more preferably the zeolitic material contains Cu and/or Zr, preferably Cu as extra-framework ions.

19. The process of embodiment 18, wherein the zeolitic material contains from 0.5 to 15 wt.-% of M as extra-framework ions calculated as the element and based on 100 wt-% of $YO_2$ contained in the zeolitic material, preferably from 1 to 12 wt.-%, more preferably from 1.3, to 9 wt.-%, more preferably from 1.5 to 7 wt.-%, more preferably from 1.8 to 5 wt.-%, more preferably from 2 to 4.5 wt.-%, more preferably from 2.3 to 4 wt.-%, more preferably from 2.5 to 3.7 wt.-%, more preferably from 2.6 to 3.5 wt.-%, more preferably from 2.7 to 3.3 wt.-%, more preferably from 2.9 to 3.1 wt.-%.

20. The process of embodiment 18 or 19, wherein the M:X$_2$O$_3$ molar ratio of the zeolitic material is in the range of from 0.05 to 2.5, preferably from 0.1 to 2, more preferably from 0.2 to 1.8, more preferably from 0.3 to 1.5, more preferably from 0.5 to 1.2, more preferably from 0.7 to 1, more preferably from 0.75 to 0.95, more preferably from 0.8 to 0.9.

21. The process of any of embodiments 1 to 20, wherein the zeolitic material contains substantially no Na, preferably substantially no Na or K, more preferably substantially no alkali metal, and more preferably substantially no alkali metal or alkaline earth metals.

22. The process of any of embodiments 1 to 21, wherein the average particle size of the zeolitic material having the MOR framework structure along the 002 axis of the crystallites is in the range of from 5±1 nm to 150±30 nm as determined by powder X-ray diffraction, wherein preferably the particle size of the zeolitic material along the 002 axis of the crystallites is in the range of from 10±1 nm to 100±15 nm, more preferably from 15±2 nm to 80±12 nm, more preferably from 20±2 nm to 70±11 nm, more preferably from 25±3 nm to 65±10 nm, more preferably from 30±3 nm to 60±9 nm, more preferably from 35±4 nm to 55±5 nm, more preferably from 40±4 nm to 50±5 nm, more preferably from 44±4 nm to 48±5 nm, and more preferably from 45±5 nm to 47±5 nm.

23. The process of any of embodiments 1 to 22, wherein the average particle size of the primary crystallites of the zeolitic material having the MOR framework structure as determined by powder X-ray diffraction is in the range of from 5±1 nm to 100±15 nm, wherein preferably the average particle size of the primary crystallites is in the range of from 10±1 nm to 90±14 nm, more preferably from 20±2 nm to 85±13 nm, more preferably from 30±3 nm to 80±12 nm, more preferably from 35±4 nm to 75±11 nm, more preferably from 40±4 nm to 70±11 nm, more preferably from 45±5 nm to 65±10 nm, more preferably from 50±5 nm to 65±10 nm, and more preferably from 55±8 nm to 65±10 nm.

24. The process of any of embodiments 1 to 23, wherein the catalyst provided in (i) comprises a zeolitic material having the MOR framework structure, wherein the zeolitic material having the MOR framework structure preferably comprises one or more zeolites selected from the group consisting of Mordenite, UZM-14, [Ga—Si—O]-MOR, Ca-Q, LZ-211, Maricopaite, Na-D, RMA-1, and mixtures of two or more thereof, wherein preferably the zeolitic material is UZM-14 and/or Mordenite, preferably Mordenite.

25. The process of any of embodiments 1 to 24, wherein the catalyst provided in (i) comprises a zeolitic material having the MFI framework structure, wherein the zeolitic material having the MFI framework structure preferably comprises one or more zeolites selected from the group consisting of Silicalite, ZSM-5, [Fe—Si—O]-MFI, Monoclinic H-ZSM-5, [Ga—Si—O]-MFI, [As—Si—O]-MFI, AMS-1B, AZ-1, Bor-C, Encilite, Boralite C, FZ-1, LZ-105, Mutinaite, NU-4, NU-5, TS-1, TSZ, TSZ-III, TZ-01, USC-4, USI-108, ZBH, ZKQ-1B, ZMQ-TB, organic-free ZSM-5, and mixtures of two or more thereof, more preferably from the group consisting of ZSM-5, AMS-1B, AZ-1, FZ-1, LZ-105, NU-4, NU-5, TSZ, TSZ-III, TZ-01, USC-4, USI-108, ZBH, ZKQ-1B, ZMQ-TB, and mixtures of two or more thereof, wherein more preferably the zeolitic material is ZSM-5.

26. The process of any of embodiments 1 to 25, wherein the catalyst provided in (i) further comprises one or more metal oxides and/or one or more metalloid oxides in addition to the zeolitic material, wherein the one or more metal oxides and/or one or more metalloid oxides are preferably selected from the group consisting of silica, alumina, titania, zirconia, lanthana, magnesia, and mixtures and/or mixed oxides of two or more thereof, more preferably from the group consisting of silica, alumina, titania, zirconia, magnesia, silica-alumina mixed oxides, silica-titania mixed oxides, silica-zirconia mixed oxides, silica-lanthana mixed oxides, silica-zirconia-lanthana mixed oxides, alumina-titania mixed oxides, alumina-zirconia mixed oxides, alumina-lanthana mixed oxides, alumina-zirconia-lanthana mixed oxides, titania-zirconia mixed oxides, and mixtures and/or mixed oxides of two or more thereof, more preferably from the group consisting of silica, alumina, silica-alumina mixed oxides, silica-zirconia mixed oxides, alumina-zirconia mixed oxides, alumina-zirconia-lanthana mixed oxides, and mixtures of two or more thereof, more preferably from the group consisting of alumina, alumina-zirconia mixed oxides, alumina-zirconia-lanthana mixed oxides, and mixtures of two or more thereof, wherein more preferably the catalyst provided in (i) further comprises silica, alumina, and/or zirconia, preferably alumina and/or zirconia, and more preferably alumina in addition to the zeolitic material.

27. The process of any of embodiments 1 to 26, wherein the framework of the zeolitic material comprised in the catalyst provided in (i) contains substantially no phosphorous, wherein preferably the zeolitic material comprised in the catalyst provided in (i) contains substantially no phosphorous, wherein more preferably the catalyst provided in (i) contains substantially no phosphorous.

28. The process of any of embodiments 1 to 27, wherein at no point prior to the contacting in (iii) of the catalyst provided in (i) with the gas stream provided in (ii) has the zeolitic material material having the MOR framework structure been subject to a treatment for the removal of X$_2$O$_3$ from its framework structure, and preferably to a treatment for the removal of X$_2$O$_3$ from the zeolitic material.

29. The process of any of embodiments 1 to 28, wherein the zeolitic material having the MOR framework structure is prepared by a process comprising (1) preparing a mixture comprising at least one source of YO$_2$, at least one source of X$_2$O$_3$, and comprising one or more organotemplates as structure directing agent;

(2) crystallizing the mixture prepared in (i) for obtaining a zeolitic material having the MOR framework structure;

(3) optionally isolating the zeolitic material obtained in (2);

(4) optionally washing the zeolitic material obtained in (2) or (3);

(5) optionally drying and/or calcining the zeolitic material obtained in (2), (3), or (4);

(6) optionally subjecting the zeolitic material obtained in (2), (3), (4), or (5) to an ion-exchange procedure, wherein extra-framework ions contained in the zeolitic material are ion-exchanged against H$^+$;

(7) optionally subjecting the zeolitic material obtained in (2), (3), (4), (5), or (6) to an ion-exchange procedure, wherein extra-framework ions contained in the zeolitic material are ion-exchanged against one or more metal ions M selected from the group consisting of alkaline earth metals and/or transition metals, preferably from the group consisting of metals selected from group 4 and groups 6 to 11 of the Periodic Table of the Elements, more preferably from group 4 and groups 8 to 11, wherein more preferably the one or more metal ions M are selected from the group consisting of Mg, Ti, Zr, Cu, Co, Cr, Ni, Fe, Mo, Mn, Ru, Rh, Pd, Ag, Os, Ir, Pt, Au, Sn, Zn, Ca, Mg and mixtures of two or more thereof, more preferably from the group consisting of Zr, Cu, Sn, Zn, Ca, Mg, and mixtures of two or more thereof, more preferably from the group consisting of Zr, Cu, Zn, and mixtures of two or more thereof, wherein more preferably the extra-framework ions contained in the zeolitic material are ion-exchanged against Cu and/or Zr, preferably Cu;

(8) optionally drying and/or calcining the zeolitic material obtained in (7).

30. The process of embodiment 29, wherein the one or more organotemplates comprised in the mixture prepared in (1) is selected from the group consisting of tetraalkylammonium containing compounds and tetraalkylphosphonium containing compounds, preferably from the group consisting of tetraalkylammonium cation $R^1R^2R^3R^4N^+$-containing compounds and tetraalkylphosphonium cation $R^1R^2R^3R^4P^+$-containing compounds, wherein $R^1$, $R^2$, $R^3$, and $R^4$ independently from one another stand for optionally substituted and/or optionally branched ($C_1$-$C_6$)alkyl, preferably ($C_1$-$C_5$)alkyl, more preferably ($C_1$-$C_4$)alkyl, more preferably ($C_1$-$C_3$)alkyl, and even more preferably for optionally substituted methyl or ethyl, wherein even more preferably $R^1$, $R^2$, $R^3$, and $R^4$ stand for optionally substituted ethyl, preferably for unsubstituted ethyl.

31. The process of embodiment 30, wherein the one or more tetraalkylammonium cation $R^1R^2R^3R^4N^+$-containing compounds and/or that the one or more tetraalkylphosphonium cation $R^1R^2R^3R^4P^+$-containing compounds are salts, preferably one or more salts selected from the group consisting of halides, preferably chloride and/or bromide, more preferably chloride, hydroxide, sulfate, nitrate, phosphate, acetate, and mixtures of two or more thereof, more preferably from the group consisting of chloride, hydroxide, sulfate, and mixtures of two or more thereof, wherein more preferably the one or more tetraalkylammonium cation $R^1R^2R^3R^4N^+$-containing compounds and/or that the one or more tetraalkylphosphonium cation $R^1R^2R^3R^4P^+$-containing compounds are hydroxides and/or bromides, and even more preferably bromides.

32. The process of any one of embodiments 29 to 31, wherein the one or more organotemplates comprised in the mixture prepared in (1) is selected from the group consisting of N,N,N,N-tetra($C_1$-$C_4$)alkylammonium and N,N,N,N-tetra($C_1$-$C_4$)alkylphosphonium compounds, preferably from the group consisting of N,N,N,N-tetra($C_1$-$C_3$)alkylammonium and N,N,N,N-tetra($C_1$-$C_3$)alkylphosphonium compounds, more preferably from the group consisting of N,N,N,N-tetra($C_1$-$C_2$)alkylammonium and N,N,N,N-tetra($C_1$-$C_2$)alkylphosphonium compounds, more preferably from the group consisting of N,N,N,N-tetra($C_1$-$C_2$) alkylammonium and N,N,N,N-tetra($C_1$-$C_2$)alkylphosphonium compounds, more preferably from the group consisting of N,N,N,N-tetraethylammonium compounds, N,N,N,N-tetramethylammonium compounds, N,N,N,N-tetraethylphosphonium compounds, N,N,N,N-tetramethylphosphonium compounds, and mixtures of two or more thereof, wherein even more preferably the one or more organotemplates comprise one or more N,N,N,N-tetraethylammonium or N,N,N,N-tetraethylphosphonium compounds, preferably one or more N,N,N,N-tetraethylammonium compounds.

33. The process of any of embodiments 29 to 32, wherein the organotemplate:$YO_2$ molar ratio of the one or more organotemplates to $YO_2$ in the mixture provided according to (1) is in the range of from 0.005 to 0.14, preferably from 0.01 to 0.3, more preferably from 0.02 to 0.2, more preferably from 0.025 to 0.14, more preferably from 0.03 to 0.1, more preferably from 0.035 to 0.08, more preferably from 0.04 to 0.06, and more preferably from 0.045 to 0.055.

34. The process of any of embodiments 29 to 33, wherein the mixture prepared in (1) and crystallized in (2) contains substantially no zeolitic material, wherein preferably the mixture prepared in (1) and crystallized in (2) contains substantially no seed crystals.

35. The process of any of embodiments 29 to 34, wherein in (6) the step of subjecting the zeolitic material to an ion-exchange procedure includes the steps of
(6.a) subjecting the zeolitic material obtained in (2), (3), (4), or (5) to an ion-exchange procedure, wherein extra-framework ions contained in the zeolitic material are ion-exchanged against $NH_4^+$;
(6.b) calcining the ion-exchanged zeolitic material obtained in (6.a) for obtaining the H-form of the zeolitic material.

36. The process of embodiment 35, wherein calcining in (5), (6.b), (8) and/or (12) is conducted at a temperature in the range of from 200 to 850° C., preferably of from 250 to 800° C., more preferably of from 300 to 750° C., more preferably of from 350 to 700° C., more preferably of from 400 to 650° C., more preferably of from 450 to 620° C., more preferably of from 500 to 600° C., more preferably of from 520 to 580° C., and more preferably of from 540 to 560° C.

37. The process of embodiment 35 or 36, wherein calcining of the zeolitic material in (5), (6.b), (8) and/or (12) is effected by calcining of the zeolitic material for a duration ranging from 0.5 to 36 h, preferably from 1 to 32 h, more preferably from 2 to 28 h, more preferably from 4 to 24 h, more preferably from 6 to 20 h, more preferably from 8 to 18 h, more preferably from 10 to 14 h, and more preferably from 11.5 to 12.5 h.

38. The process of any of embodiments 29 to 37, wherein in (7) the zeolitic material is ion-exchanged such as to obtain a loading of the one or more metal ions M in the zeolitic material ranging from 0.5 to 15 wt.-% calculated as the one or more elements M and based on 100 wt.-% of $YO_2$ contained in the zeolitic material, preferably from 1 to 12 wt.-%, more preferably from 1.3 to 9 wt.-%, more preferably from 1.5 to 7 wt.-%, more preferably from 1.8 to 5 wt.-%, more preferably from 2 to 4.5 wt.-%, more preferably from 2.3 to 4 wt.-%, more preferably from 2.5 to 3.7 wt.-%, more preferably from 2.6 to 3.5 wt.-%, more preferably from 2.7 to 3.3 wt.-%, and more preferably from 2.9 to 3.1 wt.-%.

39. The process of any of embodiments 29 to 38, wherein Y is selected from the group consisting of Si, Sn, Ti, Zr, Ge, and combinations of two or more thereof, Y preferably being Si.

40. The process of any of embodiments 29 to 39, wherein the at least one source for $Y_2$ comprises one or more compounds selected from the group consisting of silicas, silicates, and mixtures thereof, preferably from the group consisting of fumed silica, silica hydrosols, reactive amorphous solid silicas, silica gel, silicic acid, water glass, sodium metasilicate hydrate, sesquisilicate, disilicate, colloidal silica, silicic acid esters, tetraalkoxysilanes, and mixtures of two or more thereof, more preferably from the group consisting of fumed silica, silica hydrosols, silica gel, silicic acid, water glass, colloidal silica, silicic acid esters, tetraalkoxysilanes, and mixtures of two or more thereof, more preferably from the group consisting of fumed silica, silica hydrosols, silica gel, colloidal silica, and mixtures of two or more thereof, more preferably from the group consisting of fumed silica, silica gel, colloidal silica, and mixtures of two or more thereof, wherein more preferably the at least one source of $YO_2$ is selected from the group consisting of fumed silica, colloidal silica, and mixtures thereof, wherein more preferably fumed silica is employed as the source of $YO_2$.

41. The process of any of embodiments 29 to 40, wherein X is selected from the group consisting of Al, B, In, Ga, and combinations of two or more thereof, X preferably being Al.

42. The process of any of embodiments 29 to 41, wherein the at least one source for $X_2O_3$ comprises one or more aluminum salts, preferably an aluminate of an alkali metal, wherein the alkali metal is preferably selected from the group consisting of Li, Na, K, Rb, and Cs, wherein more preferably the alkali metal is Na and/or K, and wherein even more preferably the alkali metal is Na.

43. The process of any of embodiments 29 to 42, wherein the $YO_2:X_2O_3$ molar ratio of the mixture prepared in (1) is in the range of from 2 to 50, preferably from 4 to 40, more preferably from 6 to 35, more preferably from 10 to 30, more preferably from 13 to 25, more preferably from 15 to 23, more preferably from 17 to 22, and more preferably from 19 to 21.

44. The process of any of embodiments 29 to 43, wherein the mixture prepared in (1) further comprises a solvent system containing one or more solvents, wherein the solvent system preferably comprises one or more solvents selected from the group consisting of polar protic solvents and mixtures thereof, preferably from the group consisting of n-butanol, isopropanol, propanol, ethanol, methanol, water, and mixtures thereof, more preferably from the group consisting of ethanol, methanol, water, and mixtures thereof, wherein more preferably the solvent system comprises water, and wherein more preferably water is used as the solvent system, preferably deionized water.

45. The process of embodiment 44, wherein the mixture prepared in (1) and crystallized in (2) comprises one or more organotemplates, and wherein the mixture prepared in (1) comprises water as the solvent system, wherein the $H_2O:YO_2$ molar ratio of the mixture prepared in (1) preferably is in the range of from 5 to 100, preferably from 10 to 80, more preferably from 20 to 70, more preferably from 25 to 65, more preferably from 30 to 60, more preferably from 35 to 55, more preferably from 37 to 50, more preferably from 39 to 47, and more preferably from 40 to 45.

46. The process of any of embodiments 29 to 45, wherein the mixture prepared in (1) further comprises one or more alkali metals (AM), preferably one or more alkali metals selected from the group consisting of Li, Na, K, Cs, and mixtures thereof, wherein more preferably the mixture prepared in (1) further comprises Na and/or K, more preferably Na as the alkali metal AM.

47. The process of embodiment 46, wherein the mixture prepared in (1) and crystallized in (2) comprises one or more organotemplates, and wherein the $AM:YO_2$ molar ratio of alkali metals to $YO_2$ in the mixture prepared in (1) is in the range of from 0.01 to 3, preferably from 0.05 to 2.5, more preferably from 0.1 to 2, more preferably from 0.2 to 1.5, more preferably from 0.3 to 1.2, more preferably from 0.35 to 1, more preferably from 0.4 to 0.9, more preferably from 0.45 to 0.8, more preferably from 0.5 to 0.7, and more preferably from 0.55 to 0.65.

48. The process of any of embodiments 29 to 47, wherein the crystallization in (2) involves heating of the mixture prepared in (1), preferably to a temperature ranging from 75 to 220° C., more preferably from 90 to 210° C., more preferably from 110 to 205° C., more preferably from 130 to 200° C., more preferably from 140 to 195° C., more preferably from 150 to 190° C., more preferably from 155 to 185° C., more preferably from 160 to 180° C., and more preferably from 165 to 175° C.

49. The process of any of embodiments 29 to 48, wherein the crystallization in (2) is conducted under autogenous pressure, preferably under solvothermal conditions, and more preferably under hydrothermal conditions.

50. The process of any of embodiments 29 to 49, wherein the mixture prepared in (1) and crystallized in (2) comprises one or more organotemplates, and wherein the crystallization in (2) involves heating of the mixture prepared in (1) for a period in the range of from 50 to 115 h, more preferably from 60 to 95 h, more preferably from 65 to 85 h, more preferably from 70 to 80 h, more preferably from 70 to 78 h, and more preferably from 75 to 77 h.

51. The process of any of embodiments 29 to 50, wherein the zeolitic material having an MOR framework structure crystallized in (2) is Mordenite.

52. The process of any of embodiments 29 to 51, wherein the mixture prepared in (1) and crystallized in (2) contains substantially no phosphorous.

53. The process of any of embodiments 29 to 52, wherein the framework of the zeolitic material obtained in (2) contains substantially no phosphorous, wherein preferably the zeolitic material obtained in (2) contains substantially no phosphorous.

54. The process of any of embodiments 29 to 53, wherein the zeolitic material obtained in (7) is not subject to a temperature of 540° C. or greater, more preferably of 520° C. or greater, more preferably of 500° C. or greater, more preferably of 450° C. or greater, more preferably of 400° C. or greater, more preferably of 350° C. or greater, more preferably of 300° C. or greater, more preferably of 250° C. or greater, more preferably of 200° C., and more preferably of 150° C. or greater.

55. The process of any of embodiments 29 to 54, the process further comprising (9) mixing the zeolitic material obtained in (2), (3), (4), (5), (6), (7) or (8) with one or more binders;

(10) kneading of the mixture obtained in (9);

(11) molding of the kneaded mixture obtained in (10) to obtain one or more moldings; and

(12) drying and/or calcining the one or more moldings obtained in (11).

56. The process of embodiment 55, wherein the one or more binders are selected from the group consisting of inorganic binders, wherein the one or more binders preferably comprise one or more sources of a metal oxide and/or of a metalloid oxide or one or more sources of graphite, wherein the one or more sources of a metal oxide and/or of a metalloid oxide are preferably selected from the group consisting of silica, alumina, titania, zirconia, lanthana, magnesia, and mixtures and/or mixed oxides of two or more thereof, more preferably from the group consisting of silica, alumina, titania, zirconia, magnesia, silica-alumina mixed oxides, silica-titania mixed oxides, silica-zirconia mixed oxides, silica-lanthana mixed oxides, silica-zirconia-lanthana mixed oxides, alumina-titania mixed oxides, alumina-zirconia mixed oxides, alumina-lanthana mixed oxides, alumina-zirconia-lanthana mixed oxides, titania-zirconia mixed oxides, and mixtures and/or mixed oxides of two or more thereof, more preferably from the group consisting of silica, alumina, silica-alumina mixed oxides, silica-zirconia mixed oxides, alumina-zirconia mixed oxides, alumina-zirconia-lanthana mixed oxides, and mixtures of two or more thereof, more preferably from the group consisting of alumina, alumina-zirconia mixed oxides, alumina-zirconia-lanthana mixed oxides, and mixtures of two or more thereof, wherein more preferably the one or more binders comprise one or more sources of silica, alumina, zirconia, and/or graphite, the one or more binders preferably comprising one or more sources of alumina and/or zirconia, preferably of alumina, wherein more preferably the binder consists of one or more sources of alumina and/or zirconia, preferably of one or more sources of alumina, wherein more preferably the binder comprises alumina and/or zirconia, preferably alumina, wherein more preferably the binder consists of alumina and/or zirconia, preferably of alumina.

57. The process of any of embodiments 1 to 56, wherein ethylene oxide and/or 2-aminoethanol comprised in the gas stream obtained in (iii) is separated from said gas stream and recycled to (ii).

EXAMPLES

The crystallite size of the samples was determined using X-ray diffraction by fitting the diffracted peak width using the software TOPAS 4.2. Instrumental broadening was considered during the peak fitting using the fundamental parameter approach as described in TOPAS 4.2 Users Manual (Bruker AXS GmbH, Östliche Rheinbrückenstr. 49, 76187 Karlsruhe, Germany). This leads to a separation of the instrumental from the sample broadening. The sample contribution was determined using a single Lorentzian profile function that is defined in the following equation:

$$\beta = \lambda/(L \cdot \cos\theta)$$

where $\beta$ is the Lorentzian full width at half maximum (FWHM), $\lambda$ is the X-ray wavelength of the CuK$\alpha$ radiation used, L is the crystallite size, and $\theta$ is the half the scattering angle of the peak position.

The crystallite size of the 002 reflection in samples having the MOR framework type was determined in a refinement of the local data surrounding the 002 reflection, from 21° to 24.2° (2θ). Single peaks with varying crystallite sizes model the surrounding reflections.

The data was collected in the Bragg-Brentano geometry from 2° to 70° (2θ), using a step size of 0.02° (2θ).

Example 1: Synthesis of Cu-Mordenite

In a 5 l plastic beaker 120 g fumed silica (CAB-O-SIL M5, Sigma-Aldrich) are suspended in 900 g deionized water. To this suspension a mixture of 52.04 g tetraethylammonium bromide (TEABr, Aldrich) in 161.7 g deionized water is added. The resulting mixture is agitated for 1 h at a stirring speed of 200 rpm. Then, a mixture of 36.5 g sodium hydroxide flakes (NaOH, Sigma-Aldrich) in 161.7 g deionized water is added. The resulting mixture is then agitated for 1.5 h at a stirring speed of 300 rpm. Subsequently, 188.6 g deionized water are added and then a mixture of 15.66 g sodium aluminate (NaAlO$_2$, Sigma-Aldrich) in 188.6 g deionized water. The resulting mixture is then agitated for 1 h at a stirring speed of 200 rpm. The pH value of the mixture was determined to be 12.2. A gel is formed which aged over night.

The synthetic gel displaying a molar composition of 0.28 Na$_2$O:0.048 Al$_2$O$_3$:SiO$_2$:44.5 H$_2$O: 0.13 TEABr is then crystallized in a pressure tight vessel for 72 h at 170° C. under agitating at a stirring speed of 250 rpm. Then, the resulting product is filtered off as a solid and washed with deionized water until the electrical conductance of the washing water reaches a value lower than 150 μS. The solids are then dried in air at 90° C. for 12 h. Subsequently, the solids are heated in air to 90° C. with a heating rate of 3.5° C. per minute and then left at said temperature for 2 h. Then the solids are heated to 120° C. with a heating rate of 1.5° C. per minute and then left at said temperature for 2 h. Then the solids are heated to 550° C. with a heating rate of 4.5° C./min and left at said temperature for 12 h. The yield was 82 g.

According to the elemental analysis the resulting product had the following contents determined per 100 g substance of <0.1 g carbon, 4.9 g aluminum, 3.2 g sodium and 37 g silicon.

The BET surface area was determined to be 404 m$^2$/g. The crystallinity of the product was measured to be 90%.

As taken from the X-ray diffraction pattern of the resulting product, the zeolitic material obtained displays the MOR framework structure as the single crystalline phase, wherein the average crystal size as calculated from the X-ray diffraction data was determined to be 59 nm, and the average crystal size along the 002 axis of the crystallites was determined to be 46 nm.

In a 2 liter stirring apparatus, 70 g of ammonium nitrate were placed as an aqueous solution (10 wt.-% NH$_4$NO$_3$), 70 g of the zeolitic material were added, and the resulting mixture was stirred for 2 h at 80° C. The zeolitic material was then filtered off and washed with 630 g of distilled water. The filtrate was discarded and a new 10-wt. % aqueous solution containing 70 g of ammonium nitrate was then placed in the stirring apparatus to which the washed zeolitic material was added and the resulting mixture again stirred for 2 h at 80° C. The zeolitic material was then filtered off and washed anew with 630 g of distilled water. The washed material was then dried for 5 h at 120° C. and subsequently calcined at 500° C. for 5 h with a heating rate of 2° C./min. The entire procedure was then repeated, affording 63.4 g of the H-form of the zeolitic material.

According to the elemental analysis, the resulting sample had the following contents determined per 100 g substance of <0.1 g carbon, 5.0 g aluminum, 0.01 g sodium and 38 g silicon.

The BET surface area was determined to be 474 m$^2$/g.

1.5 liters of a 0.01 molar aqueous solution of copper(II) acetate (3 grams in 1.5 liters) were placed in a 2 liter stirring apparatus and 25 g of the H-form of the zeolitic material were then added and the mixture stirred at room temperature for 20 h. The zeolitic material was then filtered off, and the filtrate was discarded. A new solution of 1.5 liters of a 0.01 molar aqueous solution of copper(II) acetate (3 grams in 1.5 liters) was then placed in the 2 liter stirring apparatus and the zeolitic material was added thereto and the mixture stirred at room temperature for 20 h. The zeolitic material was then filtered off, the filtrate discarded, and the zeolitic material was again added to a new solution of 1.5 liters of a 0.01 molar aqueous solution of copper(II) acetate (3 grams in 1.5 liters) and stirred for 20 h at room temperature. The resulting product was then separated from the solution by centrifugation, the solution discarded, and the zeolitic material subsequently suspended in 1.25 liters of distilled water. The zeolitic material was then separated from the solution by centrifugation, the washwater was discarded, and the washing procedure with distilled water was repeated 3 times for washing the zeolitic material. The zeolitic material was then dried for 24 h at 110° C., thus affording 24.4 g of a copper-exchanged zeolitic material.

According to the elemental analysis the resulting product had the following contents determined per 100 g substance of <0.1 g carbon, 4.8 g aluminum (0.096 mol), 2.6 g copper (0.041 mol) and 35 g silicon.

The BET surface area was determined to be 371 m²/g.

Example 2: Synthesis of H-Mordenite

In a stirring apparatus, 2.4 kg fumed silica (CAB-O-SIL M5, Sigma-Aldrich) are suspended in 18 kg deionized water. To this suspension a solution of 1.04 kg tetraethylammonium bromide (TEABr, Aldrich) in 1.04 kg deionized water is added. The resulting mixture is agitated for 1 h at a stirring speed of 150 rpm. Then, a solution of 0.73 kg sodium hydroxide flakes (NaOH, Sigma-Aldrich) in 3.5 kg deionized water is added. The resulting mixture is then agitated for 1.5 h at a stirring speed of 180 rpm. Subsequently, a solution of 0.31 kg sodium aluminate ($NaAlO_2$, Sigma-Aldrich) in 4 kg deionized water is added, together with 3 kg of deionized water used to wash the receptacle containing the previous solution. The resulting mixture is then agitated for 1 h at a stirring speed of 180 rpm. The pH value of the resulting gel was determined to be 13.1. The gel was then aged over night.

The synthetic gel displaying a molar composition of 0.5 $Na_2O$:0.0475 $Al_2O_3$:$SiO_2$:44.5 $H_2O$:0.125 TEABr is then heated under stirring at 200 rpm to 170° C. in a pressure tight vessel and held at that temperature for 84 h at 170° C. under further stirring at the same speed. Then, the resulting product displaying a pH of 12.5 is filtered off as a solid and washed five times with 50 liters of deionized water, respectively, until the electrical conductance of the washing water reaches a value of 85 µS. The filter cake is then heated to 100° C. and a nitrogen stream is conducted over the filter cake for 16 h for drying at that temperature. 1.667 kg of a crystalline material was thus obtained, which is then calcined for 12 h at 550° C., thus obtaining 1.533 kg of a white powder.

According to the elemental analysis the resulting product had the following contents determined per 100 g substance of <0.1 g carbon, 5.3 g aluminum, 3.2 g sodium and 35 g silicon.

The BET surface area was determined to be 400 m²/g. The crystallinity of the product was measured to be 93%.

As taken from the X-ray diffraction pattern of the resulting product displayed in FIG. 1, the zeolitic material obtained displays the MOR framework structure as the single crystalline phase. The average crystal size of the crystallites as calculated from the X-ray diffraction data was determined to be 57.5 nm.

In a stirring apparatus, 650 g of ammonium nitrate were placed as a solution in 5.85 kg of distilled water (10 wt.-% $NH_4NO_3$), 650 g of the calcined zeolitic material were added to the solution, and the resulting mixture was heated to 80° C. under stirring and held at that temperature for 2 h. The zeolitic material was then filtered off, the filtrate was discarded, and a new 10-wt. % aqueous solution containing 650 g of ammonium nitrate was then placed in the stirring apparatus to which the filtered-off zeolitic material was added and the resulting mixture again stirred for 2 h at 80° C. The zeolitic material was then filtered off and washed with 12 liters of distilled water. The washed material was then dried for 5 h at 120° C. and subsequently calcined at 500° C. for 5 h to afford a white powder.

According to the elemental analysis, the resulting sample had the following contents determined per 100 g substance of <0.1 g carbon, 5.4 g aluminum, 0.1 g sodium and 40 g silicon.

A new 10-wt. % aqueous solution containing 650 g of ammonium nitrate was then placed in the stirring apparatus, and the calcined powder was added to the solution, after which the resulting mixture was heated to 80° C. under stirring and held at that temperature for 2 h. The zeolitic material was then filtered off and washed with 12 liters of distilled water. The washed material was then dried for 5 h at 120° C. and subsequently calcined at 500° C. for 5 h to afford the H-form of the zeolitic material.

According to the elemental analysis, the resulting sample had the following contents determined per 100 g substance of <0.1 g carbon, 5.0 g aluminum (0.185 mol), 0.01 g sodium and 38 g silicon (1.36).

The BET surface area was determined to be 438 m²/g.

Example 3: Synthesis of UZM-14-B According to U.S. Pat. No. 7,687,423 B2

In a 2 l plastic beaker 91 g fumed silica (CAB-O-SIL M5, Sigma-Aldrich) are provided. In a separate plastic beaker, 960 g of deionized water are weighed in, and 15.63 g of sodium hydroxide (NaOH, Sigma-Aldrich), 11.28 g of sodium aluminate ($NaAlO_2$, Sigma-Aldrich), and 12.65 g tetraethylammonium bromide (TEABr, Aldrich) are added and stirring and the mixture is further stirred until complete dissolution thereof is achieved. The solution is then added to the beaker containing the fumed silica under stirring for providing a viscous gel, which is further stirred for 2 h. The synthesis gel thus obtained (1.07 kg) displaying a molar composition of 0.2 $Na_2O$:0.051 $Al_2O_3$:$SiO_2$:39.5 $H_2O$:0.045 TEABr is then distributed among several pressure tight vessels and then crystallized for 76 h at 150° C. under agitating at a stirring speed of 300 rpm. The resulting product is then filtered off as a solid, washed with deionized water, and dried, followed by a step of heating the solids under a nitrogen atmosphere with a heating rate of 2° C. per minute to 540° C. and calcining the material at said temperature for 2 h, after which calcination at that temperature is continued in air for an additional 5 h. The yield was 59.1 g.

According to the elemental analysis the resulting product had the following contents determined per 100 g substance of <0.1 g carbon, 4.7 g aluminum, 2.8 g sodium and 38 g silicon.

The BET surface area was determined to be 416 m²/g. The crystallinity of the product was measured to be 80%.

As taken from the X-ray diffraction pattern of the resulting product displayed in FIG. 1, the zeolitic material obtained displays the MOR framework structure as the single crystalline phase. The average crystal size as calculated from calculated from the X-ray diffraction data was determined to be 47.5 nm, and the average crystal size along the 002 axis of the crystallites was determined to be 33 nm.

In a 2 liter stirring apparatus, 50 g of ammonium nitrate dissolved in 450 g of distilled water were placed as an aqueous solution (10 wt.-% $NH_4NO_3$), 50 g of the zeolitic material were added, and the resulting mixture was stirred for 2 h at 80° C. The zeolitic material was then filtered off and a new 10-wt. % aqueous solution containing 50 g of ammonium nitrate dissolved in 450 g of distilled water was then placed in the stirring apparatus to which the filtered off zeolitic material was added and the resulting mixture again stirred for 2 h at 80° C. The zeolitic material was then filtered off and washed with distilled water until the wash water was free of nitrate. The washed material was then dried for 4 h at 120° C. and subsequently calcined at 500°

C. in air for 5 h. The entire procedure was then repeated, affording 40.8 g of the H-form of the zeolitic material.

According to the elemental analysis, the resulting sample had the following contents determined per 100 g substance of 4.2 g aluminum, <0.01 g sodium and 38 g silicon.

The BET surface area was determined to be 486 m$^2$/g. The crystallinity of the product was measured to be 71%, and the average crystal size as calculated from calculated from the X-ray diffraction data was determined to be 47 nm, and the average crystal size along the 002 axis of the crystallites was determined to be 33 nm.

Comparative Example 1: Synthesis of H-Mordenite Containing Phosphorus 100 g of the zeolitic material obtained from Example 2 was placed in a beaker and a solution of 19.64 g of phosphoric acid (85%) dissolved in 100 ml of distilled water was then added thereto and the resulting mixture was homogenized with a spatula. After a short period, the mixture became viscous, and was subsequently dried in a drying oven at 110° C. for 12 h. The dried mixture was then heated to 500° C. in air at a rate of 2° C./min and was then calcined at that temperature for 5 hours for affording 106.5 g of H-Mordenite containing phosphorus.

According to the elemental analysis the resulting product had the following contents determined per 100 g substance of <0.1 g carbon, 4.3 g aluminum, 4.1 g of phosphorus, and 36 g silicon.

The BET surface area was determined to be 141 m$^2$/g.

Comparative Example 2: Synthesis of Cu-Mordenite Containing Phosphorus 900 g of distilled water were placed in a 5 L beaker, and 120 g of silica (CAB-O-SIL M5) were added thereto under stirring to form a suspension. A solution of 52.04 g of tetraethylammonium bromide (TEABr) dissolved in 161.7 g of distilled water was then added to the suspension and the resulting mixture was stirred for 1 h at 200 rpm. A solution of 36.5 g of NaOH dissolved in 161.7 g of distilled water were then added thereto and the mixture stirred 1.5 h at 300 rpm. 188.6 g of distilled water were then added to the mixture under stirring followed by addition of a solution of 15.66 g NaAlO$_2$ dissolved in 188.6 g distilled water, and the resulting mixture was stirred for 1 h at 200 rpm. The resulting gel displayed a pH of 12.2 and was allowed to stand overnight for aging thereof. The aged gel was then placed in an autoclave and crystallized under stirring (250 rpm) at 170° C. for 72 h. The resulting solid product was filtered of and washed with distilled water to electroneutrality (<150 μS). The solid was then dried in air at 90° C. for 2 h, and then at 120° C. for 2 h, after which the dried material was then heated to 550° C. at a rate of 4.5° C./min and was then calcined at that temperature for 12 hours for affording 50.5 g of H-Mordenite According to the elemental analysis the resulting product had the following contents determined per 100 g substance of <0.1 g carbon, 4.7 g aluminum, 3.1 g of sodium, and 34 g silicon.

A solution of 45 g ammonium nitrate dissolved in 405 g distilled water were placed in a mixing apparatus, and 45 g of the H-Mordenite were added thereto under stirring. The mixture was then heated to 80° C. and stirred at that temperature for 2 h. The solution was then replaced with a fresh solution of 45 g ammonium nitrate dissolved in 405 g distilled water and stirred anew for 2 h at 80° C. The solution was then again replaced with a fresh solution of 45 g ammonium nitrate dissolved in 405 g distilled water and stirred anew for 2 h at 80° C., after which the solution was again replaced and stirred anew for 2 h at 80° C. The solid was then isolated by suction filtration and washed with distilled water until it was free of nitrate. The resulting solid was then dried at 120° C. for 5 h, and subsequently heated to 500° C. at a rate of 2° C./min and calcined at that temperature for 5 h for affording 40.6 g of ammonium-exchanged Mordenite.

According to the elemental analysis the resulting product had the following contents determined per 100 g substance of <0.1 g carbon, 5.1 g aluminum, 0.03 g of sodium, and 39 g silicon.

1.5 L of a 0.01 M solution of copper (II) acetate in distilled water were placed in a 2 L round bottom flask, and 15 g of the ammonium-exchanged Mordenite was added thereto under stirring, after which the mixture was stirred for 20 h at room temperature. The solution was then exchanged against a fresh solution of copper (II) acetate in distilled water (0.01 M), and the mixture was stirred anew for 2 h, after which the solution was again exchanged against a fresh solution of copper (II) acetate in distilled water (0.01 M) and stirred for 20 h. The solid product was separated by centrifugation and then suspended in 750 ml of distilled water, after which it was separated by centrifugation. The washing step with distilled water and separation by centrifugation was repeated three times, after which the solid product was dried at 110° C. for 24 h for affording 14.4 g of H-Mordenite.

According to the elemental analysis the resulting product had the following contents determined per 100 g substance of 4.7 g aluminum, 2.6 g of copper, and 35 g silicon.

10 g of the H-Mordenite was placed in a beaker and a solution of 6.53 g of phosphoric acid dissolved in 4 ml of distilled water was then added thereto and the resulting mixture was homogenized with a spatula. After a short period, the mixture became viscous, and was subsequently dried in a drying oven at 110° C. for 12 h. The dried mixture was then heated to 500° C. in air at a rate of 2° C./min and was then calcined at that temperature for 5 hours for affording 14.4 g of H-Mordenite containing phosphorous.

According to the elemental analysis the resulting product had the following contents determined per 100 g substance of <0.1 g carbon, 3.3 g aluminum, 1.9 g of copper, 12.3 g of phosphorus, and 24.8 g silicon.

Example 4: Synthesis of H-ZSM-5

Na-ZSM-5 Synthesis

In a 2 m$^3$ reactor 79.61 kg of de-ionised water is first introduced. To the water, 411.15 kg of an aqueous tetrapropylammonium hydroxide solution (TPAOH; 40 wt. %) was added under stirring (70 rpm). The suspension is let for stirring for another 10 min. 8.2 kg solid NaOH is added slowly in 2.5 kg portions under stirring and after each portion the system is allowed to mix for 5 minutes. Next, 29.25 kg aluminium triisopropoxide is added to the suspension and the system is stirred for another 1 h. At the end, 538.19 kg colloidal silica (Ludox AS-40) is added followed by additional 10 kg of de-ionized water. The synthesis mixture is stirred another 1 h at room temperature before the reactor is flushed with nitrogen gas and the pressure reduced to −900 mbar. Afterwards the reactor is heated to 170° C. in 11 h. The hydrothermal synthesis is run for 72 h at 170° C. under 70 rpm stirring. After crystallization the synthesis mixture is cooled down to 30° C. The suspension is transferred to a larger vessel where the pH of the suspension is adjusted to 7±0.5, by addition of a 10 wt. % aqueous nitric acid solution. The pH adjusted suspension is let for stirring for another 30 min at 70 rpm. The zeolite is separated by filtration and the filter cake is washed with de-ionised water until a conductivity of the wash water <200 μS. The filtercake is then dried at 120° C. for 96 h. The dried material was calcined to 550° C. in air for 6 h for obtaining a calcined ZSM-5 zeolite with a BET surface area of 390 m$^2$/g, and displaying a crystallinity as determined by X-ray diffraction of 94%.

250 kg de-ionized water is added to a 400 L reactor and 25 kg ammonium nitrate is added under stirring (150 rpm). The suspension is heated to 80° C., followed by the addition of 25 kg of the calcined zeolite. The mixture is stirred further for 1 h at 80° C. Afterwards the reaction mixture is cooled down and filtered off using a filterpress and washed with water until a conductivity in the wash water <200 μS. The ion-exchange process is then repeated for obtaining an ammonium-exchanged ZSM-5. The filter cake obtained after the second ammonium ion-exchange process is dried for 10 h at 120° C. and calcined at 500° C. in air for 5 h (heating rate 2° C./min) for obtaining H-ZSM-5.

According to the elemental analysis the resulting product had the following contents determined per 100 g substance of <0.1 g carbon, 1.6 g aluminum, <0.01 g of sodium, and 43 g silicon.

The BET surface area was determined to be 408 m$^2$/g.

Example 5: Preparation of a Shaped Body with H-Mordenite and Zirconia-Binder 50 g of H-Mordenite obtained from Example 2 is admixed with 2.5 g of Walocel (Wolf Walsrode AG PUFAS Werk KG) and 28.95 g of ZrOH(OAc)$_3$ (Fa. Aldrich; 20% ZrO$_2$) in a kneader for 5 min, after which 45 ml of distilled water are added under kneading and the mixture is further kneaded for a total kneading time of 45 min. Extrudates with a diameter of 2 mm are then formed from the kneaded mixture, and the extrudates are then heated to 120° C. at a heating rate of 3° C./min and then dried at that temperature for 6 h, after which the extrudates are further heated to 500° C. at a heating rage of 2° C./min and then calcined in air at that temperature for 5 h. 42.3 g of extrudate are obtained, displaying a piled weight of 420 g/L.

Example 6: Preparation of a Shaped Body with H-Mordenite and Alumina-Binder 50 g of H-Mordenite obtained from Example 2 is admixed with 12.5 g of boehmite alumina (Pural SB, 20% ZrO$_2$; Sasol) in a kneader for 5 min. 1.88 ml of nitric acid (65%) is then added, together with 10 ml of distilled water, and the mixture kneaded for a further 10 min, after which 2.5 g of Walocel (Wolf Walsrode AG PUFAS Werk KG) are added followed by the addition of 30 ml of water, after which the mixture is further kneaded for a total kneading time of 45 min. Extrudates with a diameter of 2 mm are then formed from the kneaded mixture, and the extrudates are then heated to 120° C. at a heating rate of 3° C./min and then dried at that temperature for 6 h, after which the extrudates are further heated to 500° C. at a heating rage of 2° C./min and then calcined in air at that temperature for 5 h. 35.7 g of extrudate are obtained, displaying a piled weight of 420 g/L and a cutting hardness of 16.3 N.

Example 7: Synthesis of Zr-MFI 568.75 g of tetraethylorthosilicate (TEOS; Merck) were placed in round bottom flask equipped with a stirring means and 30.87 g of a solution of 70 wt.-% Zr(IV)propoxide in 1-propanol (Aldrich) were slowly added thereto during 30 min while stirring with the aid of a dropping funnel. 500 g of tetrapropylammonium hydroxide (TPAOH) and 500 g of distilled water were then added to the mixture and the resulting mixture was stirred for 1 h. For removing propanol which was formed, 368.6 g of a propanol containing distillate were then distilled off at 95° C., after which the mixture was then allowed to cool to room temperature, and 369 g of distilled water corresponding to the weight of the distillate which had been removed was added to the reaction mixture. The mixture was then transferred to an autoclave and crystallized at 175° C. for 48 h. The resulting reaction mixture was then diluted with the same volume of water, after which the pH of the resulting mixture was adjusted to pH=7.5 using 5% HNO$_3$, and the resulting precipitate filtered off via centrifugation. The resulting solid was dried at 110° C. for 24 h and subsequently heated to 500° C. at a rate of 2° C./min and calcined at that temperature for 5 h.

According to the elemental analysis the resulting product had the following contents determined per 100 g substance of <0.1 g carbon, 3.5 g zirconium, and 43 g silicon.

The BET surface area was determined to be 517 m$^2$/g.

Example 8: Catalyst Testing

The zeolitic materials to be tested were respectively admixed with 3 wt.-% graphite and homogenized by shaking and mixing, if necessary using a mortar and pestle. The homogenized mixture is then pelletized using a 13 mm diameter pelletizing tool set applying 10-40 kN of force depending on the zeolite in order to obtain stable pellets and thus a stable target fraction, wherein the pellets obtained are 2-3 mm in height and have a diameter of 13 mm. The pellets thus obtained were then precrushed with mortar and pestle and sieved through a 1000 μm analytical sieve. Crushing and sieving was repeated for obtaining the desired target fraction having a particle diameter in the range of from 315-500 μm using suitable analytical sieves and a pestle, and wherein the fines (<315 μm) were removed by sieving on a sieving tool (e.g. Retsch AS 200) or by sieving manually.

This gas vapor stream is fed to a reactor filled with 1 cm$^3$ of catalyst particles that are of the size in the range of 315-500 μm. The catalyst bed has a diameter of 4 mm and a length of 80 mm. Due to the low diameter of the catalyst bed it is isothermal. Before the catalyst bed the gas vapor stream is heated to the reaction temperature by passing it through an inert bed. Both the catalyst bed and the inert bed are heated externally to the reaction temperature. Downstream to the catalyst bed the product stream is diluted and cooled to 250° C. Further downstream its composition is measured by an online-GC.

Results were calculated by referencing the ratio of educt to internal standard (IS) to the same ratio as obtained by analyzing the gas vapor stream from a by-pass tubing. Thus undetected products (high-boilers, coke) are taken into account as well. The following formulas give the detailed procedure:

Conversion: $X(\text{educt})=1-c(\text{educt})/c(\text{IS})/(c(\text{educt\_by-pass})/c(\text{IS-by-pass}))$ Yields: $Y(\text{product})=c(\text{product})/c(\text{IS})/(c(\text{educt\_by-pass})/c(\text{IS-by-pass}))$ Selectivities: $S(\text{product})=Y(\text{product})/X(\text{educt})$ For the standard experiment the following testing conditions were chosen: gas hourly space velocity (GHSV) of 5000 h$^{-1}$ with ethylene oxide concentration of 1 vol.-% and a pressure of 10 bar. Apart from the main educt ethylene oxide the gas stream consisted of 40 vol.-% ammonia and 1 vol.-% methane as internal standard with nitrogen as balance. The catalysts were heated in nitrogen to the reaction temperature of 300° C. and then the gas feed was switched to testing conditions. The results obtained from catalytic testing performed on Examples 1-7 and Comparative Examples 1 and 2 are displayed in Table 1 below, wherein the respective yields of monoethanolamine and ethylenediamine and the conversion rate of ethylene oxide are respectively shown in %. As regards the results obtained for Example 1, values are indicated as obtained from 2 different runs.

pared to the MFI zeolite catalyst of Example 4, a certain yield of ethylendiamine was observed, however to the detriment of the yield in monoethanolamine which was somewhat lower.

Thus, in summary, it has surprisingly been found that a highly active and selective catalyst is provided according to the present invention which allows for the direct amination of ethylene oxide to ethylenediamine and monoethanolamine.

LIST OF THE CITED PRIOR ART REFERENCES

U.S. Pat. No. 4,918,233
CN 1962058 A

TABLE 1

Results obtained from the reaction of ethylene oxide and ammonia catalyzed by samples as obtained from Examples 1-7 and from Comparative Examples 1 and 2, respectively.

| Sample | Structure | Cu [wt.-%] | Zr [wt.-%] | P | binder | EO conversion [%] | MEOA yield [%] | EDA yield [%] | MEOA + EDA yield [%] |
|---|---|---|---|---|---|---|---|---|---|
| Ex. 1 | MOR | 2.6 | — | no | — | 87 | 17.5 | 13.0 | 30.5 |
|  |  |  |  |  |  | 85 | 18.0 | 13.3 | 31.3 |
| Ex. 2 | MOR | — | — | no | — | 73 | 18.5 | 12.4 | 30.9 |
| Ex. 3 | MOR | — | — | no | — | 60 | 18.1 | 10.0 | 28.1 |
| Comp. Ex. 1 | MOR | — | — | yes | — | blocked | blocked | blocked | blocked |
| Comp. Ex. 2 | MOR | 1.9 | — | yes | — | 32 | 0.6 | ~0 | ~0.6 |
| Ex. 4 | MFI | — | — | no | — | n.a. | 30.6 | 0.2 | 30.8 |
| Ex. 5 | MOR | — | — | no | ZrO$_2$ | 83 | 65.1 | 5.1 | 70.2 |
| Ex. 6 | MOR | — | — | no | Al$_2$O$_3$ | 94 | 19.7 | 11.5 | 31.2 |
| Ex. 7 | MFI | — | 3.5 | no | — | 91 | 23.6 | 1.5 | 25.1 |

As may be taken from the results displayed in Table 1, high yields of both monoethanolamine and ethylenediamine at high conversion rates of ethylene oxide may be obtained using the inventive catalysts. In this respect, the addition of copper to the MOR zeolite catalyst in Example 1 led not only to an improvement in selectivity toward ethylenediamine compared to the MOR zeolite catalysts in Examples 2 and 3, but in particular to a considerable increase in the ethylene oxide conversion rate. The addition of phosphorous to the MOR zeolite catalysts in Comparative Examples 1 and 2, on the other hand, led to practically no conversion to either monoethanolamine or ethylenediamine, even in the presence of copper in Comparative Example 2.

The use of a binder for the MOR zeolite catalysts, on the other hand, led to different results, depending on the type of binder used. Thus, when using alumina as a binder in the MOR zeolite catalyst of Example 6, a considerable increase in the ethylene oxide conversion rate is observed, whereas the yields in monoethanolamine and ethylenediamine remained substantially unchanged. The use of zirconia as a binder in the MOR zeolite catalyst of Example 5, on the other hand, led to a tremendous increase in the yield of monoethanolamine as well as to the total yield of ethylenediamine and monoethanolamine, however to the detriment of the ethylenediamine yield which was reduced by more than half.

As regards the MFI zeolite catalyst of Example 4, the yield of monoethanolamine was considerably higher than for the MOR zeolite catalysts of Examples 2 and 3. The yield of ethylenediamine, on the other hand, was very low for the MFI zeolite catalyst of Example 4. The Zr-doped MFI zeolite of example of Example 7, on the other hand, displayed a very high ethylene oxide conversion rate, even compared to the MOR zeolite catalysts, wherein as com- JP H0687797 A
JP H07247245 A
CN 101215239 B
CN 101406845 A
CN 102974393 A
CN 103007984 A
CN102233272 A
CN102190588 A
inaugural thesis "Heterogeneous Transition Metal Catalyzed Amination of Aliphatic Diols" from Achim Fischer, Diss. ETH No 12978, 1998
WO 2009/083580 A1
U.S. Pat. No. 4,918,233
CN 101215239 A
U.S. Pat. No. 4,939,301
Feng, R. et al. in Catalysis Communications 2010, Volume 11, Issue 15, pages 1220-1223
U.S. Pat. No. 8,309,771 B2
U.S. Pat. No. 7,687,423 B2
DD 298 636 A5

The invention claimed is:
1. A process for the conversion of ethylene oxide to 2-aminoethanol and ethane-1,2-diamine comprising
  (i) providing a catalyst comprising a zeolitic material comprising YO$_2$ and X$_2$O$_3$, wherein Y is a tetravalent element and X is a trivalent element;
  (ii) providing a gas stream comprising ethylene oxide and ammonia;
  (iii) contacting the catalyst provided in (i) with the gas stream provided in (ii) for converting ethylene oxide to 2-aminoethanol and ethane-1,2-diamine, wherein in (i) the zeolitic material has the MOR framework structure.

2. The process of claim 1, wherein the gas stream provided in (ii) and contacted with the catalyst in (iii) contains ethylene oxide in an amount in the range of from 0.05 to 10 vol.-%.

3. The process of claim 1, wherein the gas stream provided in (ii) and contacted with the catalyst in (iii) contains ammonia in an amount in the range of from 5 to 90 vol.-%.

4. The process of claim 1, wherein the gas stream provided in (ii) and contacted with the catalyst in (iii) further contains hydrogen in an amount in the range of from 0.1 to 70 vol.-%.

5. The process of claim 1, wherein the gas stream provided in (ii) and contacted with the catalyst in (iii) contains 1 vol.-% or less of hydrogen.

6. The process of claim 1, wherein the gas stream provided in (ii) is heated to a temperature in the range of front 250 to 600° C., prior to contacting with the catalyst in (iii) at that temperature.

7. The process of claim 1, wherein Y is selected from the group consisting of Si, Sn, Ti, Zr, Ge, and mixtures of two or more thereof.

8. The process of claim 1, wherein X is selected from the group consisting of Al, B, In, Ga, and mixtures of two or more thereof.

9. The process of claim 1, wherein the zeolitic material is in the H-form and contains protons as extra-framework ions, wherein 0.1 wt.-% or less of the extra-framework ions are metal cations, calculated as the element and based on 100 wt.-% of $YO_2$ contained in the zeolitic material.

10. The process of claim 1, wherein the zeolitic material contains substantially no Na.

11. The process of claim 1, wherein the average particle size of the zeolitic material having the MOR framework structure along the 002 axis of the crystallites is in the range of from 5±1 nm to 150±30 ran as determined by powder X-ray diffraction.

12. The process of claim 1, wherein the zeolitic material having the MOR framework structure is prepared by a process comprising (1) preparing a mixture comprising at least one source of $YO_2$, at least one source of $X_2O_3$, and comprising one or more organotemplates as structure directing agent;

(2) crystallizing the mixture prepared in (i) for obtaining a zeolitic material having the MOR framework structure;

(3) optionally isolating the zeolitic material obtained in (2);

(4) optionally washing the zeolitic material obtained in (2) or (3);

(5) optionally drying and/or calcining the zeolitic material obtained in (2), (3), or (4);

(6) optionally subjecting the zeolitic material obtained in (2), (3), (4), or (5) to an ion-exchange procedure, wherein extra-framework ions contained in the zeolitic material are ion-exchanged against $H^+$;

(7) optionally subjecting the zeolitic material obtained in (2), (3), (4), (5), or (6) to an ion-exchange procedure, wherein extra-framework ions contained in the zeolitic material are ion-exchanged against one or more metal ions M selected from the group consisting of alkaline earth metals and/or transition metals;

(8) optionally drying and/or calcining the zeolitic material obtained in (7).

13. The process of claim 12, wherein in (6) the step of subjecting the zeolitic material to an ion-exchange procedure includes the steps of (6.a) subjecting the zeolitic material obtained in (2), (3), (4), or (5) to an ion-exchange procedure, wherein extra-framework ions contained in the zeolitic material are ion-exchanged against $NH_4^+$;

(6.b) calcining the ion-exchanged zeolitic material obtained in (6.a) for obtaining the H-form of the zeolitic material.

14. The process of claim 1, wherein ethylene oxide and/or 2-aminoethanol comprised in the gas stream obtained in (iii) is separated from said gas stream and recycled to (ii).

* * * * *